United States Statutory Invention Registration [19]

[11] Reg. Number: H533

Kimura et al. [43] Published: Oct. 4, 1988

[54] METHOD OF FORMING A COLOR IMAGE

[76] Inventors: Keizo Kimura; Shigeki Yokoyama; Tadahisa Sato, all of Fuji Photo Film Co., Ltd., 210, Nakanuma, Minami ashigara-shi, Kanagawa, Japan

[21] Appl. No.: 41,252

[22] Filed: Apr. 22, 1987

[30] Foreign Application Priority Data

Apr. 22, 1986 [JP] Japan ..... 61-93098

[51] Int. Cl.[4] ..... G03C 7/30; G03C 7/38

[52] U.S. Cl. ..... 430/386; 430/387; 430/558; 430/551

[58] Field of Search ..... 430/386, 387, 551, 558, 430/376

[56] References Cited

U.S. PATENT DOCUMENTS

| | | | |
|---|---|---|---|
| 3,725,067 | 4/1973 | Bailey et al. | 430/558 |
| 3,996,054 | 12/1976 | Santemma et al. | 430/377 |
| 4,559,297 | 12/1985 | Seto et al. | 430/558 |
| 4,576,910 | 3/1986 | Hirano et al. | 430/558 |
| 4,681,835 | 7/1987 | Ishikawa et al. | 430/386 |

FOREIGN PATENT DOCUMENTS

| | | | |
|---|---|---|---|
| 158446 | 9/1985 | Japan . | |
| 1158334 | 7/1986 | Japan | 430/386 |

*Primary Examiner*—John F. Terapane
*Assistant Examiner*—Susan Wolffe

[57] ABSTRACT

A method of forming a color image comprising developing an imagewise exposed silver halide color photographic material with a developing solution containing an aromatic primary amine developing agent in the presence of at least one coupler represented by the following formula (I) or (II):

(I)

(II)

wherein $R_1$ represents a substituted or unsubstituted alkoxy group, an unsubstituted amino group, a substituted or unsubstituted alkylamino group, a substituted or unsubstituted arylamino group, or a substituted or unsubstituted N-alkylarylamino group; $R_2$ represents a monovalent substituent; $R_3$ represents a hydrogen atom, a substituted or unsubstituted alkyl group, or a substituted or unsubstituted aryl group, or $R_1$ and $R_3$ are taken together to form a ring; Z represents an oxygen atom, an imino group, or a sulfur atom; and X represents a hydrogen atom or a monovalent substituent capable of being split off upon a coupling reaction with an oxidation product of an aromatic primary amine developing agent. The magneta color image forming coupler represented by formula (I) or (II) provides a magenta color image having high sensitivity and gradation as well as the hue of which is easily controllable. A silver halide color photographic material containing the magenta image forming coupler is also disclosed.

41 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHOD OF FORMING A COLOR IMAGE

FIELD OF THE INVENTION

The present invention relates to a method of forming a color image using a silver halide color photographic material and, particularly, to a method of forming a color image using a silver halide color photographic material, which provides a magenta color image having improved sensitivity and gradation (γ), the hue of which is easily controllable. More specifically, the present invention relates to a method of forming a color image comprising developing an imagewise exposed silver halide color photographic material with a developing solution containing an aromatic primary amine developing agent in the presence of a 1H-pyrazolo[1,5-b]-1,2,4-triazole or 1H pyrazolo[5,1-c]-1,2,4-triazole magenta coupler having a substituted nitrogen atom at the 6-position thereof.

BACKGROUND OF THE INVENTION

Almost all of magenta color image forming couplers which have been widely used in the art are 5-pyrazolones. It is known that the dyes formed upon the coupling of 5-pyrazolone type couplers with the oxidation products of aromatic primary amine developing agents have an undesirable subsidiary absorption of the yellow component in the region around 430 nm which causes color turbidity.

In order to reduce the yellow component, a pyrazolobenzimidazole nucleus, as described in British Pat. No. 1,047,612; an indazolone nucleus, as described in U.S. Pat. No. 3,770,447; and a pyrazolo[5,1-c]-1,2,4-triazole nucleus, as described in U.S. Pat. No. 3,725,067, have been proposed as a magenta color image forming coupler skeleton. However, the magenta couplers described in these patents are still insufficient because they provide only poor color images when they are mixed with a silver halide emulsion in the form of a dispersion in a hydrophilic protective colloid such as gelatin, they have a low solubility in an organic solvent having a high boiling point, they are difficult to synthesize, or the light-fastness of dyes formed therefrom is very poor.

The above-described problems have been solved by the development of magenta couplers having a 1H-pyrazolo[1,5-b]-1,2,4-triazole nucleus as described in Japanese Patent Application (OPI) No. 171956/84 (the term "OPI" as used herein means "unexamined published patent application") and U.S. Pat. No. 4,540,654. The above-described 1H-pyrazolo[1,5-b]-1,2,4-triazole magenta couplers have many features in that they provide color images which do not have an undesirable absorption of the yellow component as formed from 5-pyrazolone type couplers, they have a sufficiently high solubility in an organic solvent having a high boiling point, they are easily synthesized, and they provide color images having good light-fastness.

However, it has been found that 1H-pyrazolo[1,5-b]-1,2,4-triazole magenta couplers having a halogen atom, an alkylthio group or an arylthio group, etc. as a coupling split-off group, which can be easily synthesized, are generally insufficient with respect to sensitivity and gradation (γ).

In order to achieve the most preferred color reproduction, it is required that the maximum absorption wavelength of the color images formed from magenta couplers have the most appropriate certain value. This value is generally present in a range from 530 nm to 570 nm, although it can be varied depending on the kind of color photographic light-sensitive materials in which the magenta couplers are employed, for example, whether the magenta couplers are used in color negative films, color reversal films, or color papers, etc., or on the values of the maximum absorption wavelength of the color images formed from cyan couplers and yellow couplers which are employed in combination with the magenta couplers. Thus, when the optimum value is selected in the range, the above-described 1H-pyrazolo[1,5-b]-1,2,4-triazole magenta couplers can provide the most preferred color reproducibility coupled with no subsidiary yellow absorption in the region around 430 nm as described above.

However, the maximum absorption wavelength of color images formed from known 1H-pyrazolo[1,5-b]-1,2,4-triazole magenta couplers is present in a very narrow range of from about 540 nm to bout 550 nm. Therefore, these known 1H-pyazolo[1,5-b]-1,2,4-triazole magenta couplers have a problem that while these couplers show a desirable color reproducibility in cases where they are employed in certain color photographic light-sensitive materials and in combination with specified cyan couplers and yellow couplers, they cannot always provide a desirable color reproducibility when they are employed in other color photographic light-sensitive materials or when they are employed in combination with other cyan couplers or yellow couplers.

The maximum absorption wavelength of color images formed from the above-described 1H-pyrazolo[5,1-c]-1,2,4-triazole magenta couplers can be controlled by the selection of an organic solvent for dispersion having a high boiling point which is utilized in order to incorporate these couplers into silver halide color photographic materials in the form of an emulsified dispersion. However, according to such a method, the degree of control is small and other problems are apt to be accompanied in that the sensitivity and gradation (γ) are decreased, stain occurs, and the light-fastness of color images formed degradates. Accordingly, known 1H-pyrazolo[1,5-b]-1,2,4-triazole magenta couplers or 1H-pyrazolo[5,1-c]-1,2,4-triazole magenta couplers are not satisfactory for obtaining color images having high sensitivity and gradation, good light-fastness, and preferred color reproducibility without the occurrence of stain.

SUMMARY OF THE INVENTION

Therefore, an object of the present invention is to provide a method of forming a color image having sufficiently high sensitivity and gradation (γ).

Another object of the present invention is to provide a method of forming a color image, in which the hue of a magenta color image to be formed is easily controllable.

A further object of the present invention is to provide a silver halide color photographic material containing a magenta coupler which provides sufficiently high sensitivity and gradation and forms a magenta color image, the hue of which can be easily controlled.

A still further object of the present invention is to provide a magenta coupler which provides sufficiently high sensitivity and gradation and forms a magenta color image, the hue of which can be easily controlled. Other objects of the present invention will become apparent from the following detailed description and examples.

These objects of the present invention are achieved by a method of forming a color image comprising developing an imagewise exposed silver halide color photographic material with a developing solution containing an aromatic primary amine developing agent in the presence of at least one coupler represented by formula (I) or (II):

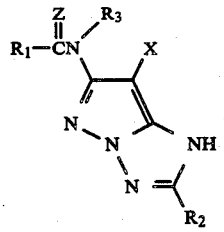

(I)

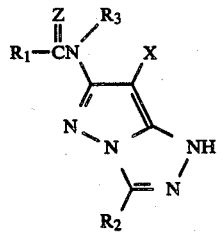

(II)

wherein $R_1$ represents a substituted or unsubstituted alkoxy group, an unsubstituted amino group, a substituted or unsubstituted alkylamino group, a substituted or unsubstituted arylamino group, or a substituted or unsubstituted N-alkylarylamino group; $R_2$ represents a monovalent substituent; $R_3$ represents a hydrogen atom, a substituted or unsubstituted alkyl group, or a substituted or unsubstituted aryl group, or $R_1$ and $R_3$ are taken together to form a ring; Z represents an oxygen atom an imino group, or a sulfur atom; and X represents a hydrogen atom or a monovalent substituent capable of being split off upon a coupling reaction with an oxidation product of an aromatic primary amine developing agent.

DETAILED DESCRIPTION OF THE INVENTION

The magenta coupler represented by formula (I) or (II) which can be used in the present invention is described in detail below.

In formula (I) or (II), $R_1$ represents an unsubstituted alkoxy group, for example, a methoxy group, an ethoxy group, an isopropoxy group, a tert-butoxy group, a hexyloxy group, etc.; an alkoxy group substituted with a substituent selectd from an alkoxy group, a halogen atom, a hydroxyl group, an aryl group, and a heterocyclic group, for example, a 2-methoxyethoxy group, a trichloromethoxy group, a trifluoromethoxy group, a 2-hydroxyethoxy group, a benzyloxy group, a tetrahydrofurfuryloxy group, etc.; an unsubstituted amino group; an unsubstituted alkylamino group, for example, a methylamino group, an octylamino group, a dimethylamino group, a diethylamino group, an N-methyl-N-octadecylamino group, an N-octyl-N-butylamino group, an N-methyl-N-phenylamino group, a dipropylamino group, a dibutylamino group, a di-2-ethylhexylamino group, a diisobutylamino group, a didodecylamino group, an octadecyl amino group, etc.; an alkylamino group substituted with a substituent selected from an alkoxy group, a hydroxyl group, and an aryl group, for example, a di-2-methoxyethylamino group, an N-methylphenethylamino group, a di-2-hydroxyethylamino group, etc.; an unsubstituted arylamino group, for example, an anilino group, a diphenylamino group, etc.; an arylamino group substituted with a substituent selected from an alkyl group, an alkoxy group, and a halogen atom, for example, a p-methylanilino group, a p-methoxyanilino group, a p-chloroanilino group, etc.; an unsubstituted N-alkylarylamino group, for example, an N-methylanilino group, an N-ethylanilino group, an N-butylanilino group, etc.; or an N-alkylarylamino group substituted with a substituent selected from an alkoxy group, a hydroxyl group, and a halogen atom, for example, an N-methyl-p-methoxyanilino group, an N-(2-hydroxyethyl)-p-chloroanilino group, etc. Of these groups for $R_1$, a methoxy group, an ethoxy group, an isopropoxy group, a tert-butoxy group, a dimethylamino group, a dipropylamino group, a dibutylamino group, a di2-hydroxyethylamino group, and a diphenylamino group, etc. are preferred, with dialkylamino groups (having preferably from 1 to 8 carbon atoms in the alkyl moiety) being particularly preferred.

In formula (I) or (II), the monovalent substituent represented by $R_2$ includes, for example, an alkyl group substituted with a sulfonamido group (for example, a sulfonamidoethyl group, a 1-methyl-2-sulfonamidoethyl group, a 3-sulfonamidopropyl group, etc.), an alkyl group substituted with an acylamino group (for example, an acylaminomethyl group, a 1-acylaminoethyl group, a 2-acylaminoethyl group, a 1-methyl-2-acylaminoethyl group, a 3-acylaminopropyl group, etc.), a phenylalkyl group substituted with a sulfonamido group (for example, a p-sulfonamidophenylmethyl group, a p-sulfonamidophenylethyl group, a 1-(p-sulfonamidophenyl)ethyl group, a p-sulfonamidophenylpropyl group, etc.), a phenylalkyl group substituted with an acylamino group (for example, a p-acylaminophenylmethyl group, a p-acylaminophenylethyl group, a 1-(p-acylaminophenyl)ethyl group, a p-acylaminophenylpropyl group, etc.), an unsubstituted alkyl group (for example, a methyl group, an ethyl group, a hexyl group, a dodecyl group, etc.), a substituted aryl group (for example, a sulfonamidophenyl group, an acylaminophenyl group, an alkoxyphenyl group, an aryloxyphenyl group, a substituted alkylphenyl group, a sulfonaminonaphthyl group, an acylaminonaphthyl group, etc.), an unsubstituted aryl group (for exax:ple, a phenyl group, a naphthyl group, etc.), etc. Of these groups for $R_2$, an alkyl group substituted with a sulfonamido group, an alkyl group substituted with an acylamino group, a phenylalkyl group substituted with a sulfonamido group, a phenylalkyl group substituted with an acylamino group, an unsubstituted alkyl group, etc. are preferred. The alkyl moiety included in these groups has preferably from 1 to 5 carbon atoms, and an ethyl group, an isopropyl group, and a tertbutyl group are particularly preferred.

In formula (I) or (II), X represents a hydrogen atom; a halogen atom (for example, a chlorine atom, a bromine atom, an iodine atom, etc.); a carboxyl group; a group bonded to the coupling position through an oxygen atom (for example, an acetoxy group, a propanoyloxy group, a benzoyloxy group, a 2,4-dichlorobenzoyloxy group, an ethoxyoxazoyloxy group, a pyruvoyloxy group, a cinnamoyloxy group, a phenoxy group, a 4-cyanophenoxy group, a 4-methanesulfonamidophenoxy group, a 4-methanesulfonylphenoxy group, an α-naphthoxy group, a 3-pentadecylphenoxy group, a benzyloxycarbonyloxy group, an ethoxy group, a 2-cyanoethoxy group, a benzyloxy group, a 2-phenethyloxy group, a 2-phenoxyethoxy group, a 5-phenyltetrazolyloxy group, a 2-benzothiazolyloxy group, etc.); a group bonded to the coupling position through a nitrogen atom (for example, a benzenesulfonamido group, an N-ethyltoluenesulfonamido group, a pentafluorobutanamido group, a 2,3,4,5,6-pentafluorobenzamido group, an octanesulfonamido group, a p-cyanophenylureido group, an N,N-diethylsulfamoylamino group, a 1-piperidyl group, a 5,5-dimethyl2,4-dioxo-3-oxazolidinyl group, a 1-benzyl-5-ethoxy-3hydantoinyl group, a 2N-1,1-dioxo-3(2H)-oxo-1,2-benzoisothiazolyl group, a 2-oxo-1,2-dihydro-1-pyridinyl group, an imidazolyl group, a pyrazolyl group, a 3,5-diethyl-1,2,4-triazol-1-yl group, a 5- or 6-bromobenzotriazol-1-yl group, a 5-methyl-1,2,3,4-tetrazol-1-yl group, a benzimidazolyl group, etc.); a group bonded to the coupling position through a sulfur atom (for example, a phenylthio group, a 2-carboxyphenylthio group, a 2-alkoxy-5-tertoctylphenylthio group (the alkoxy group having preferably from 1 to 8 carbon atoms, with a butoxy group being particularly preferred), a 4-methanesulfonylphenylthio group, a 4-octanesulfonamidophenylthio group, a benzylthio group, a 2-cyanoethylthio group, a 1-ethoxycarbonyltridecylthio group, a 5-phenyl-2,3,4,5-tetrazolylthio group, a 2-benzothioazolyl group, etc.); etc.

In formula (I) or (II), $R_3$ represents a hydrogen atom; an unsubstituted alkyl group, for example, a methyl group, an ethyl group, an isopropyl group, a hexyl group, an octyl group, an n-dodecyl group, an n-hexadecyl group, etc., with those having from 1 to 4 carbon atoms being preferred; an alkyl group substituted with a substituent selected from an alkoxy group, a halogen atom, and an aryl group, for example, a 2-methoxyethyl group, a 2chloroethyl group, a benzyl group, etc.; an unsubstituted aryl group, for example, a phenyl group, a naphthyl group, etc.; or an aryl group substituted with a substituent selected from a halogen atom and a nitro group, for example, a p-chlorophenyl group, a p-nitrophenyl group, etc. Of these groups for $R_3$, a hydrogen atom, a methyl group, an ethyl group, an isopropyl group, a hexyl group, an n-dodecyl group, an n-hexadecyl group, etc. are preferred.

In formula (I) or (II), Z represents an oxygen atom, an imino group, or a sulfur atom. An oxygen atom is particularly preferred for Z.

Of the compounds represented by formula (I) or (II), those represented by formula (I) are particularly preferred.

The coupler represented by formula (I) or (II) may also be a polymer coupler including a dimer or more.

When the moiety represented by formula (I) or (II) is included in a vinyl monomer, $R_1$ or $R_2$ may represent a linking group. Such a linking group includes an alkylene group including a substituted alkylene group (for example, a methylene group, an ethylene group, a 1,10-decylene group, $—CH_2CH_2OCH_2CH_2—$, etc.), a phenylene group including a substituted phenylene group (for example, a 1,4-phenylene group, a 1,3-phenylene group,

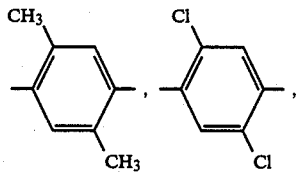

etc.), —NHCO—, —CONH—, —O—, —OCO—, an aralkylene group (for example,

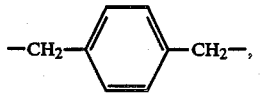

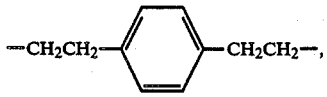

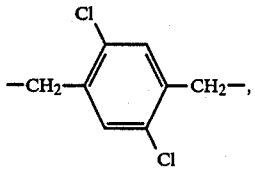

etc.), or a combination thereof.

Specific examples of preferred linking groups are $—CH_2CH_2—$,

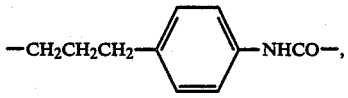

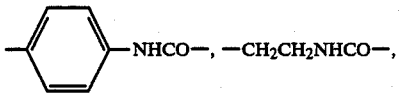

$—CH_2CH_2—O—\underset{\underset{O}{\|}}{C}—$, $—CH_2CH_2O—CH_2CH_2—NHCO—$, and

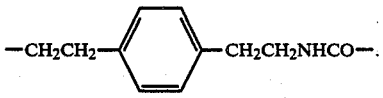

A vinyl group in the vinyl monomer may further have a substituent in addition to the coupler moiety represented by formula (I) or (II). Preferred examples of such a substituent include a chlorine atom or a lower alkyl group having from 1 to 4 carbon atoms (for example, a methyl group, an ethyl group, etc.), etc.

The monomers including the coupler moiety represented by formula (I) or (II) may form a polymer only composed of these monomers, or may form a copolymer composed of these monomers and non-color forming ethylenically unsaturated monomers which do not undergo coupling with the oxidation products of aromatic primary amine developing agents.

Examples of non-color forming monomers which do not undergo coupling with the oxidation products of aromatic primary amine developing agents include acrylic acids (for example, acrylic acid, α-chloroacrylic acid, an α-alkylacrylic acid such as methacrylic acid, etc.), esters or amides derived from these acrylic acids (for example, acylamide, n-butylacrylamide, tert-butylacrylamide, diacetoneacrylamide, methacrylamide, methyl acrylate, ethyl acrylate, n-propyl acrylate, n-butyl acrylate, t-butyl acrylate, isobutyl acrylate, 2-ethylhexyl acrylate, n-octyl acrylate, lauryl acrylate, methyl methacrylate, ethyl methacrylate, n-butyl methacrylate, α-hydroxy methacryate, etc.), methylene bisacylamide, vinyl esters (for example, vinyl acetate, vinyl propionate, vinyl laurate, etc.), acrylonitrile, methacrylonitrile, aromatic vinyl compounds (for example, styrene and derivatives thereof, e.g., vinyltoluene, divinylbenzene, vinylacetophenone, sulfostyrene, etc.), itaconic acid, citraconic acid, crotonic acid, vinylidene chloride, vinylalkyl ethers (for example, vinylethyl ether, etc.), maleic acid, maleic anhydride, maleic acid esters, N-vinyl-2-pyrrolidone, N-vinylpyridine, 2- or 4-vinylpyridine, etc. Two or more non-color forming ethylenically unsaturated monomers described above can be used together. For example, combinations of n-butyl acrylate and methyl acrylate, styrene and methacrylic acid, methacrylic acid and acrylamide, methyl methacrylate and diacetonearylamide, etc. can be employed.

The non-color forming ethylenically unsaturated monomer which is used to copolymerize with a solid water-insoluble monomer coupler can be selected so that the copolymer to be formed possesses good physical properties and/or chemical properties, for example, solubility, compatibility with a binder such as gelatin in a photographic colloid composition, flexibility, heat stability, etc., as is well known in the field of polymer color couplers.

Polymer couplers which can be used in the present invention may be water-soluble couplers or water-insoluble couplers. Particularly, polymer couplers in the form of a latex are preferably used.

Specific examples of the representative magneta couplers according to the present invention are set forth below, but the present invention should not be construed as being limited thereto.

M-1

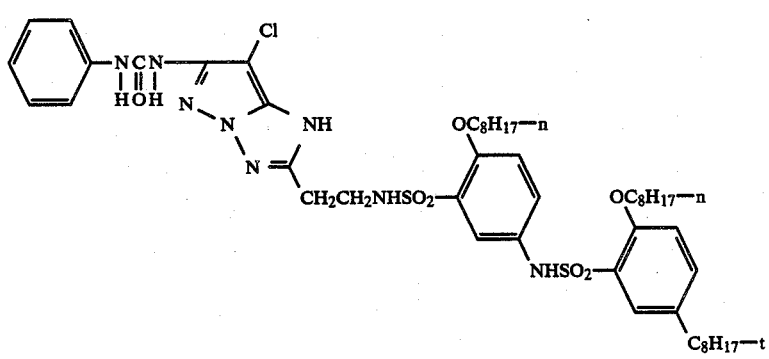

M-2

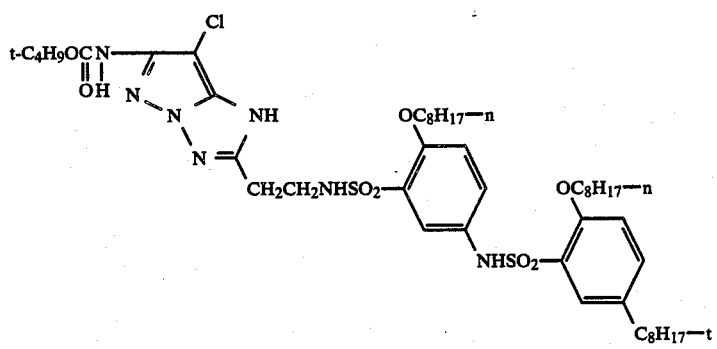

M-3

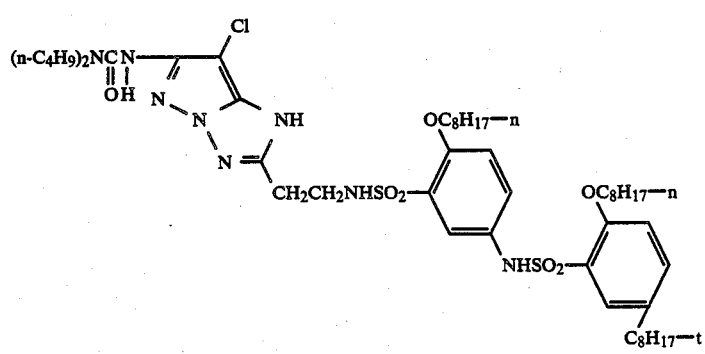

-continued
M-4
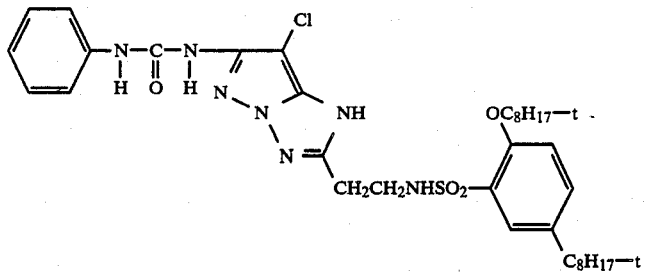
M-5
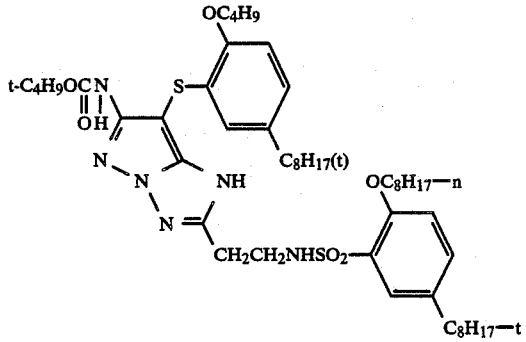
M-6
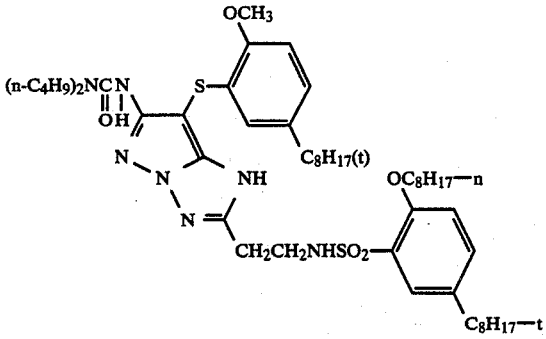
M-7
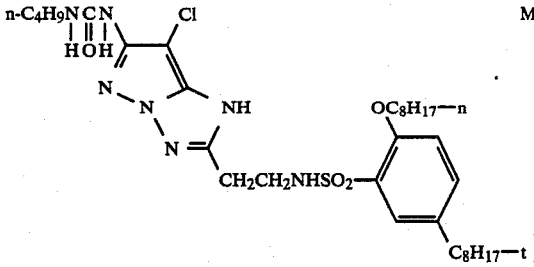
M-8
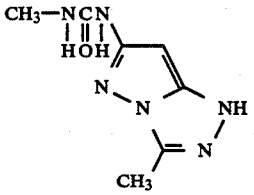
M-9
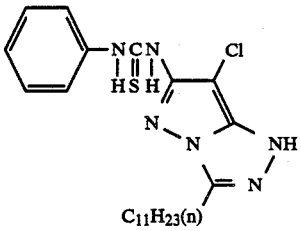
M-10
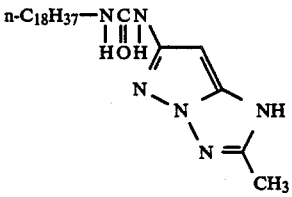
M-11
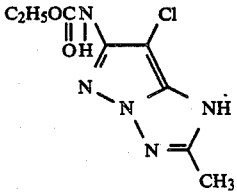
M-12
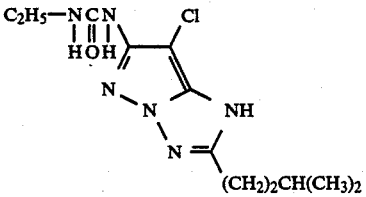
M-13
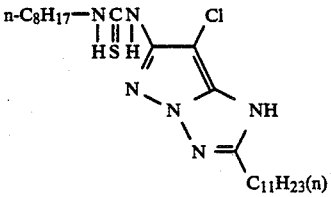

-continued
M-14
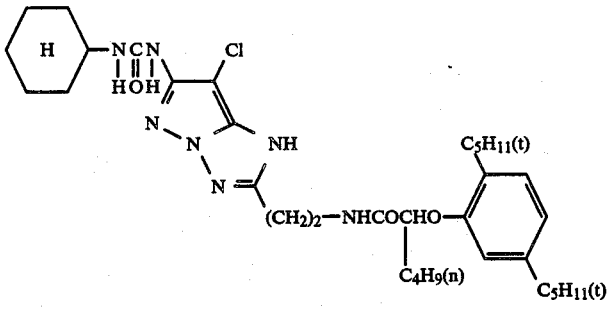
M-15
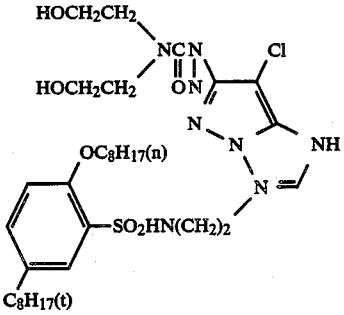
M-16
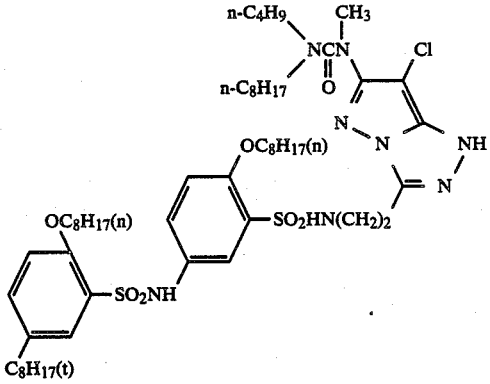
M-17
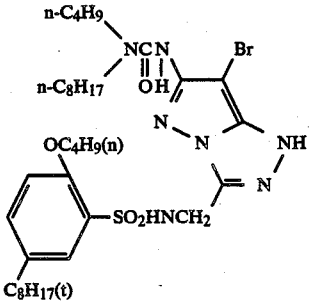
M-18
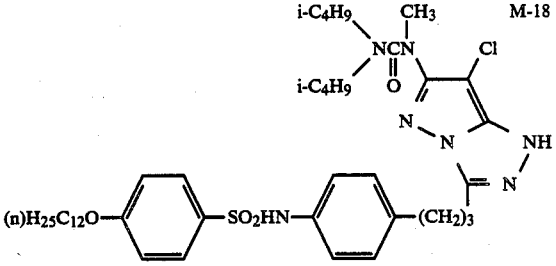
M-19
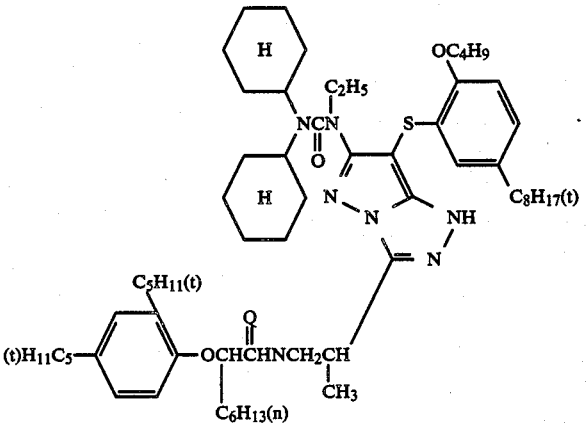

-continued
M-20
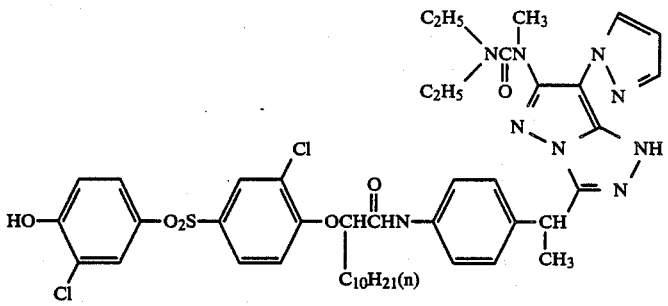
M-21
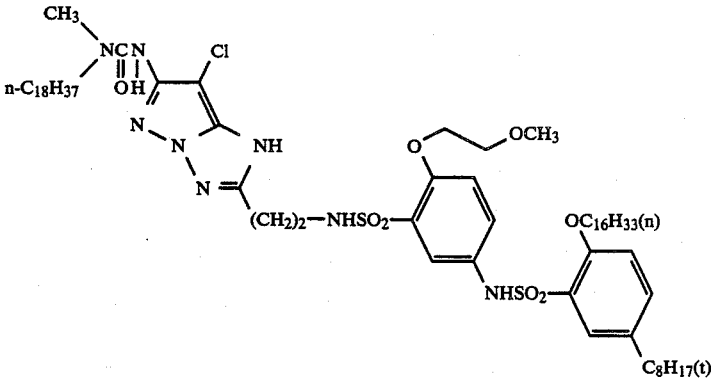
M-22
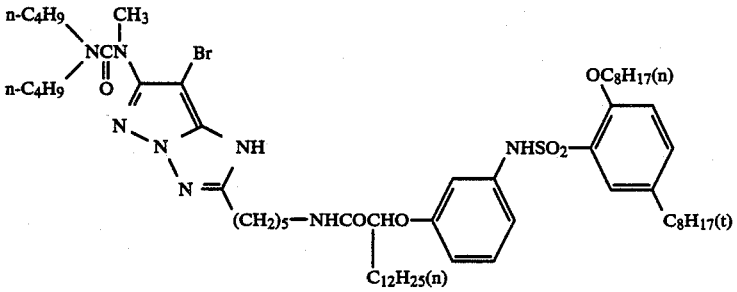
M-23
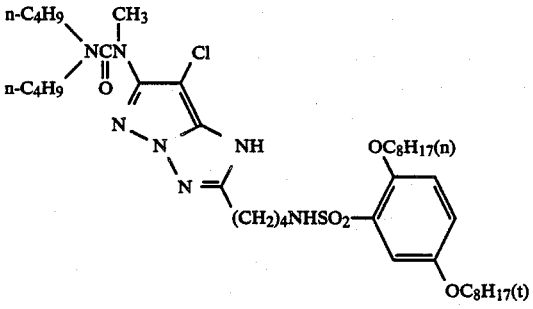
M-24
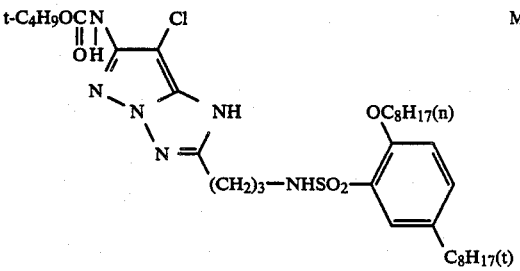
M-25
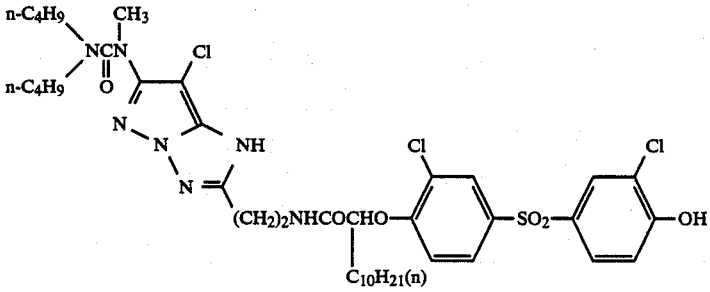

-continued
M-26
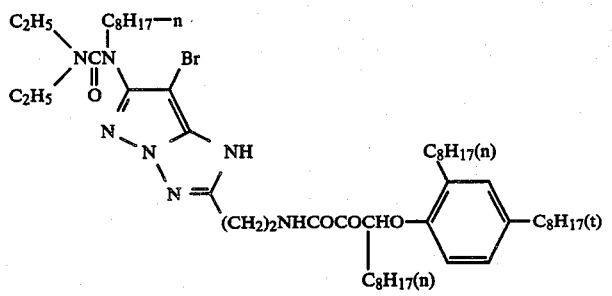
M-27
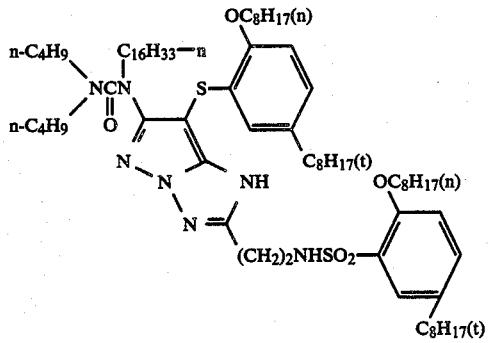
M-28
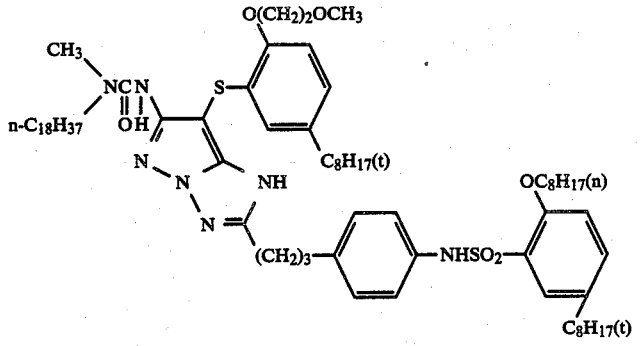
M-29
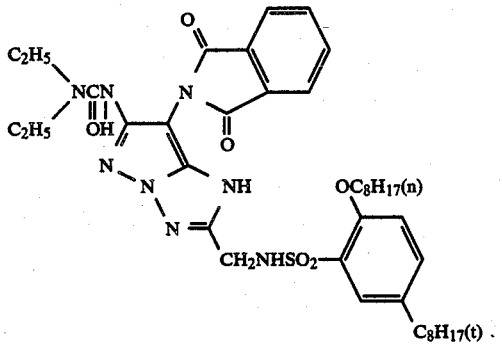
M-30
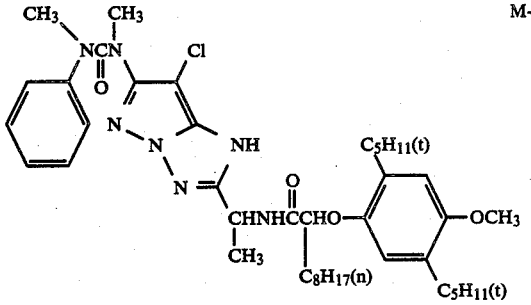
M-31
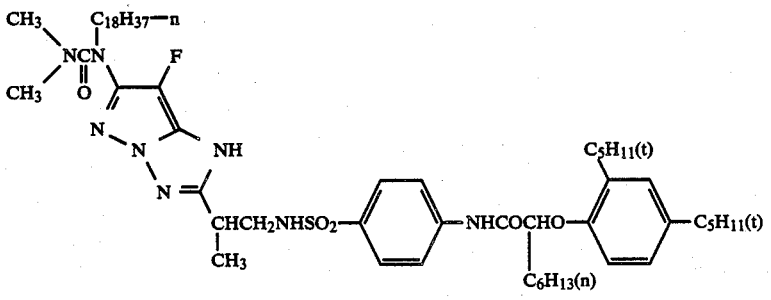

-continued
M-32
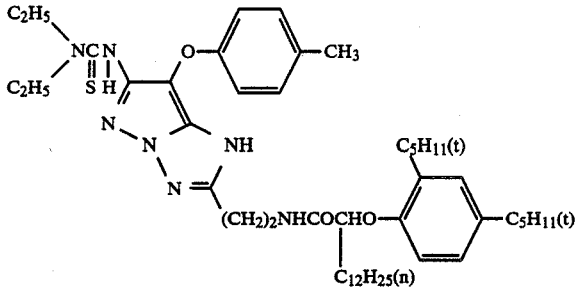
M-33
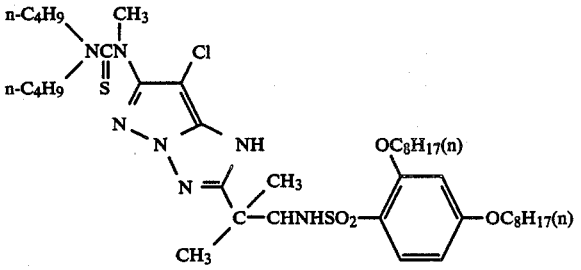
M-34
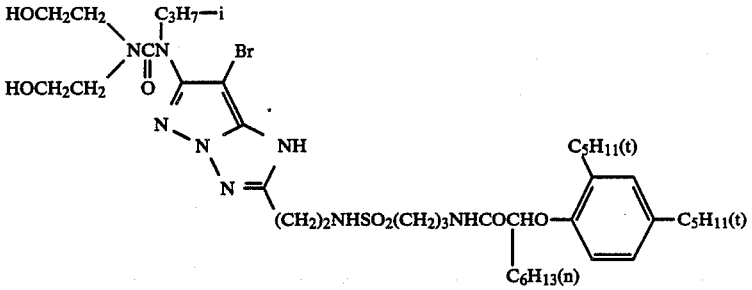
M-35
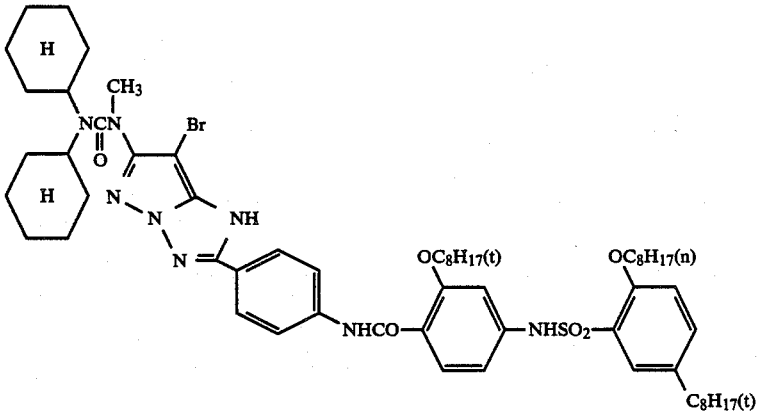
M-36
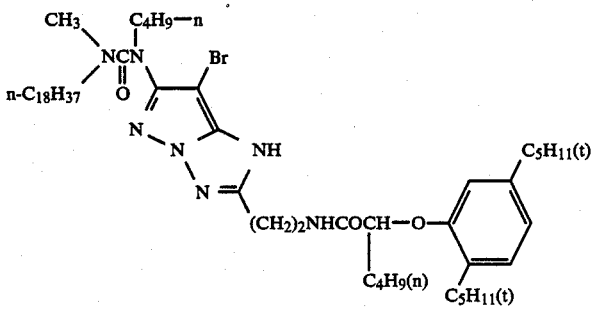

-continued
M-37
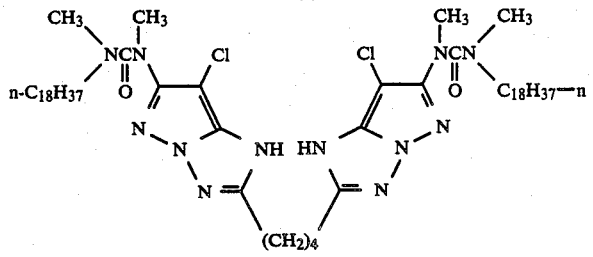
M-38
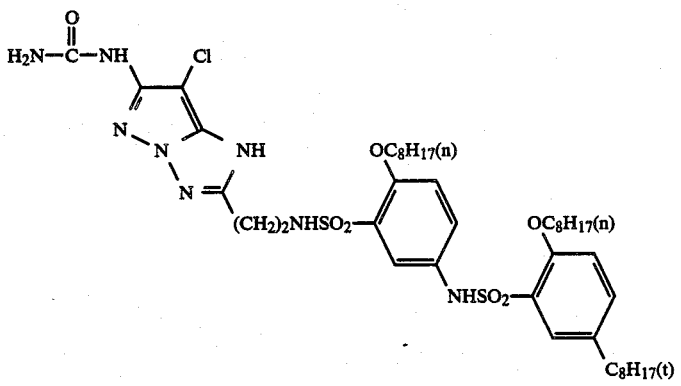
M-39
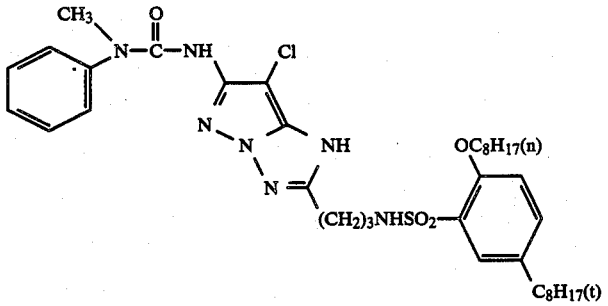
M-40
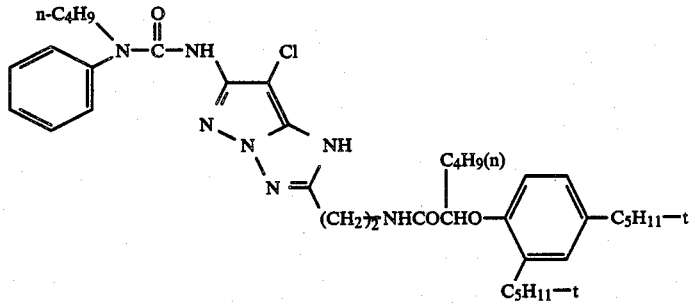
M-41
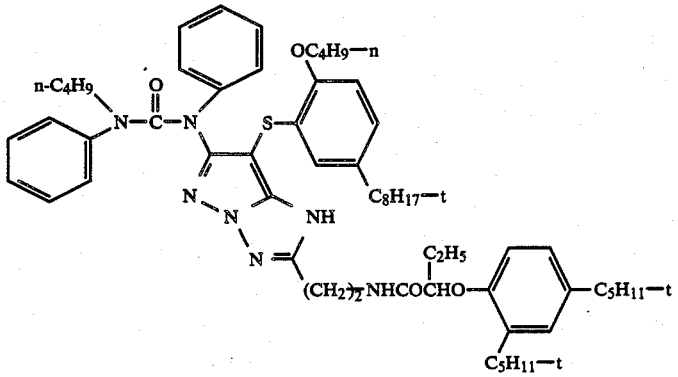

-continued
M-42
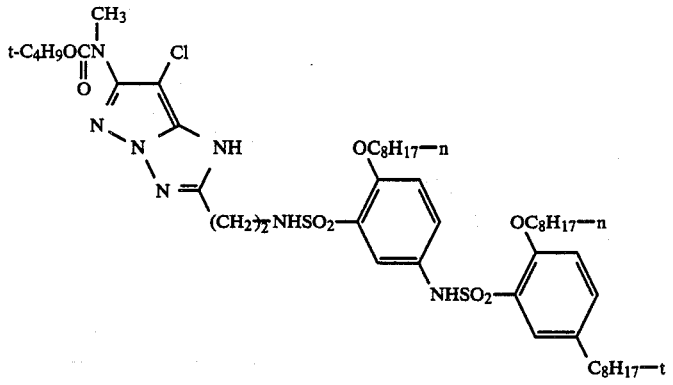
M-43
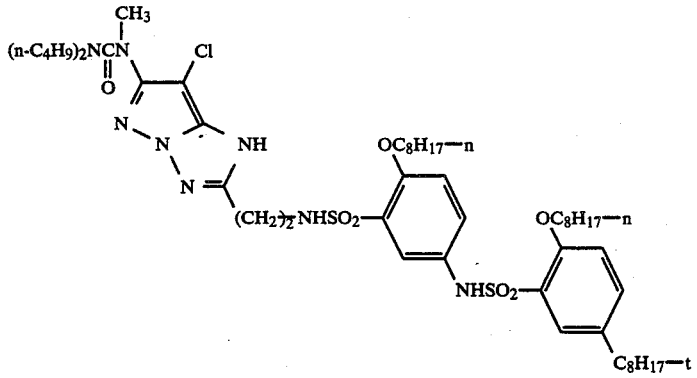
M-44
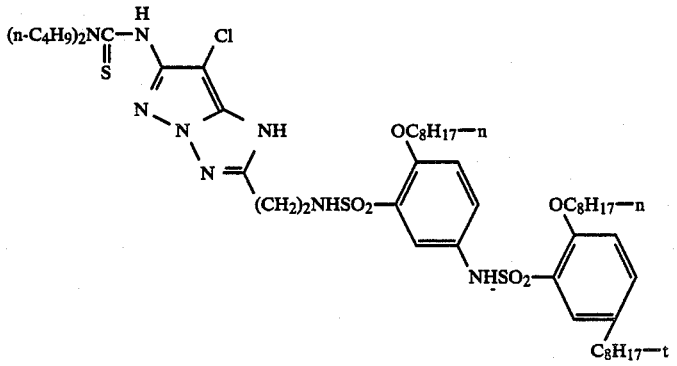
M-45
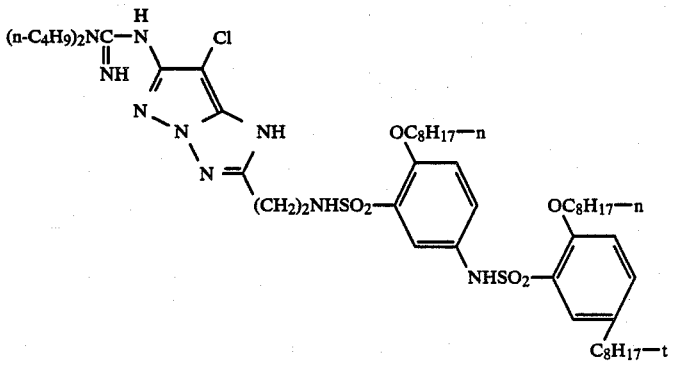

-continued
M-46
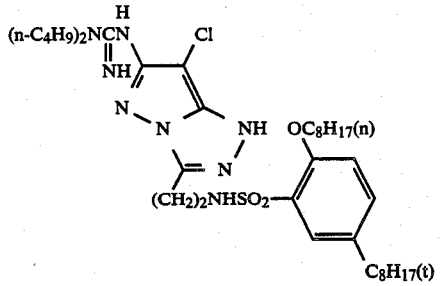
M-47
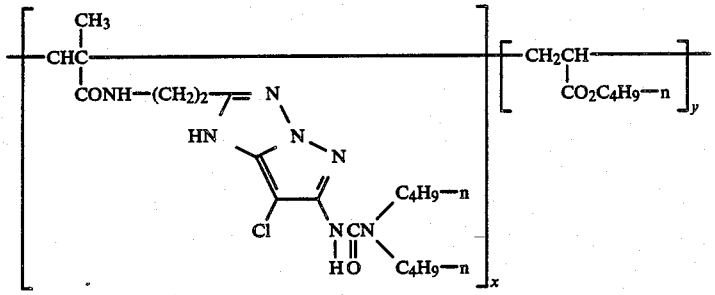
x:y = 50:50 (by weight)
M-48
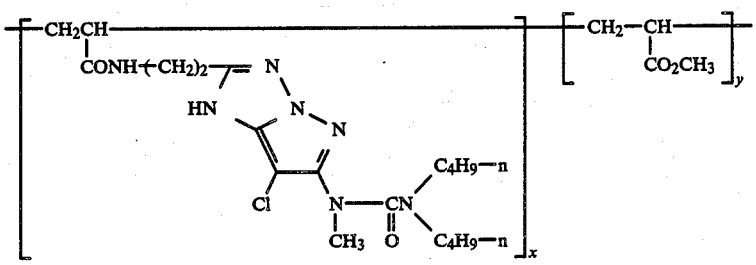
x:y = 45:55 (by weight)
M-49
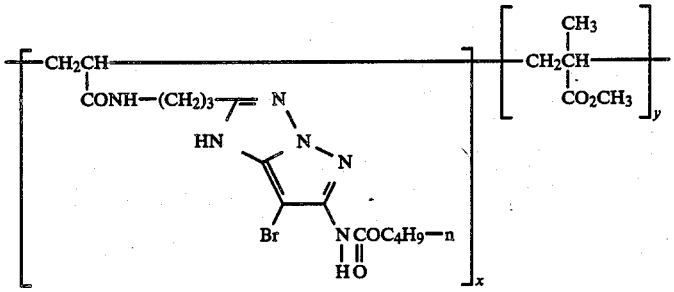
x:y = 45:55 (by weight)
M-50
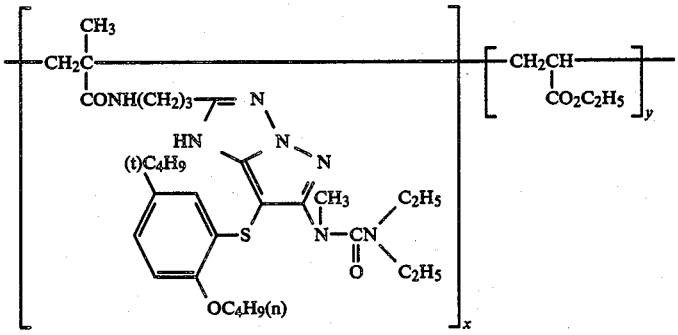
x:y = 50:50 (by weight)

-continued
M-51
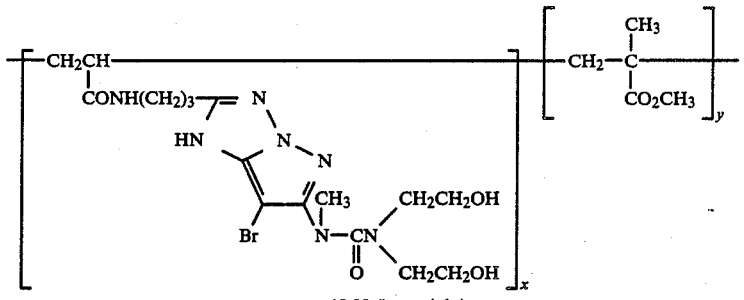
x:y = 45:55 (by weight)
M-52
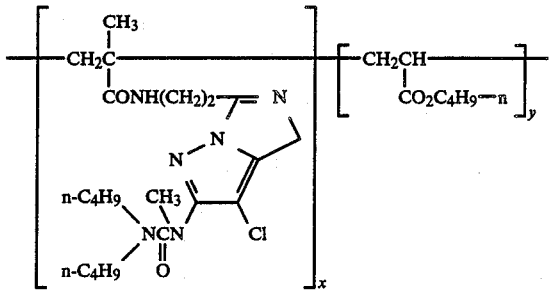
x:y = 50:50 (by weight)
General synthesis methods of the couplers according to the present invention are illustrated below.
Method 1
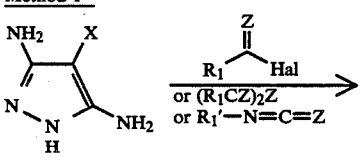
(A)
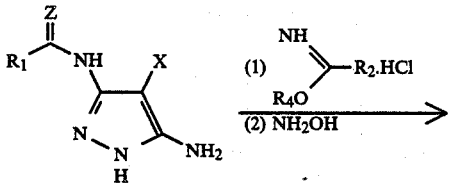
(B)
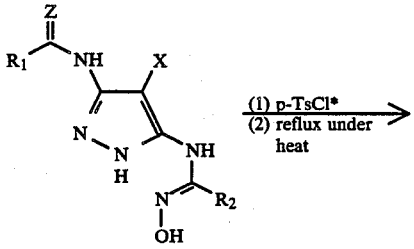
(C)
-continued
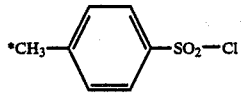
Method 2
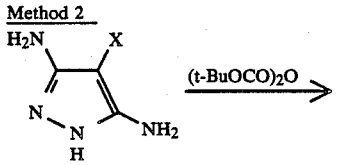
(A)
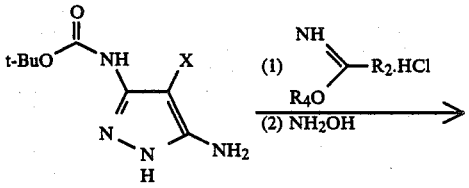
(E)
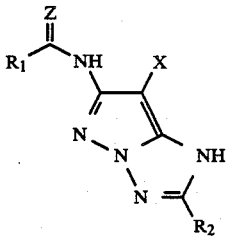
(D)

-continued
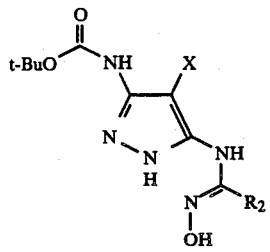
(F)
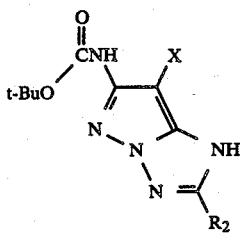
(G)
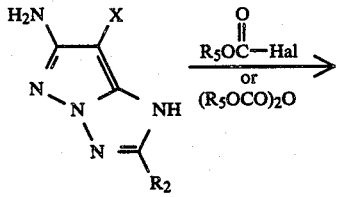
(H)
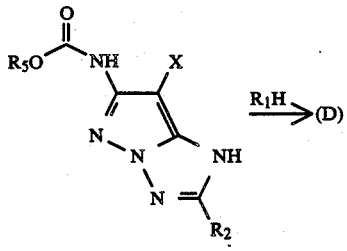
(I)
Method 3
(cases wherein $R_3$ is not a hydrogen atom)
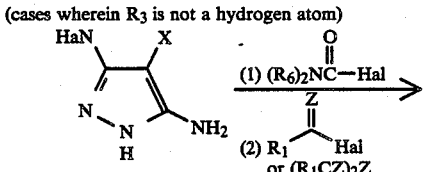
(A)
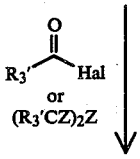
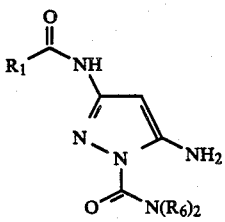
(J)
-continued
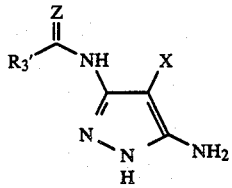
(K)
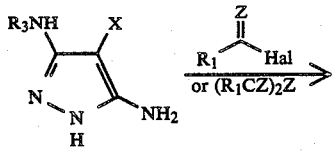
(L)
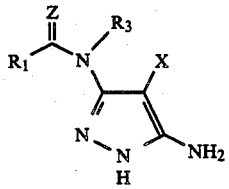
(M)
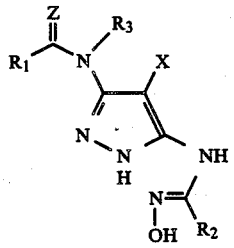
(N)
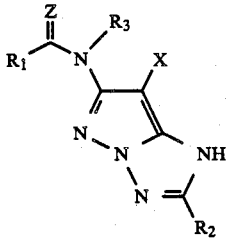
(O)
Method 4
(M) (including the case of $R_3$ = H)
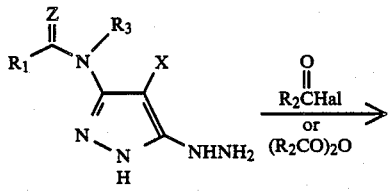
(P)

-continued

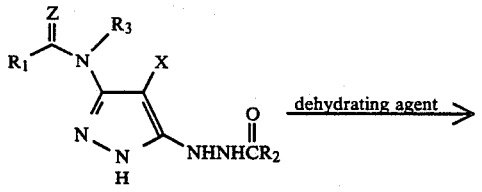

(Q)

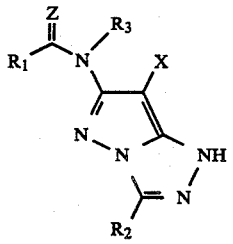

(R)

In the formulae with respect to Methods 1 to 4 shown above, $R_1$, $R_2$, $R_3$, X, and Z each has the same meaning as defined above; and $R_1'$ and $R_3'$ represent groups having the relations of $R_1$=—$NHR_1'$ and $R_3$=—$CH_2R_3'$, respectively; and $R_4$, $R_5$, and $R_6$ each represents a substituted or unsubstituted aryl group.

The methods described above are further explained below. 3,5-Diaminopyrazole represented by formula (A) wherein X is H can be synthesized by the methods as described in *J. Org. Chem.*, Vol. 33, page 2606 (1968) and *J. Prakt. Chem.*, Vol. 320, page 533 (1978). However, a method by which only one of the nitrogen atoms is subjected to ureidation, urethanation, or acylation to prepare the compounds represented by formulae (B), (E), and (K), respectively has not been known. As the result of various investigations, it has been found that the desired compound can easily be obtained according to the reaction of the compound of formula (A) with two equivalents of the above-described reagent, followed by alkaline treatment, or according to the reaction of the compound of formula (A) with one equivalent of an N,N-dialkylcarbamic chloride, preferably N,N-dimethylcarbamic chloride, to protect the nitrogen atom at the 1-position of the pyrazole ring (see the compound of formula (J) in Method 3) and, then, the reaction of the latter compound with the above-described reagent, followed by alkaline treatment. The formation of a pyrazolotriazole ring from the compound of formulae (B), (E), or (M) can be conducted using the method as described in Japanese Patent Application (OPI) No. 197688/85. While Method 2 involves a larger number of steps than Method 1, Method 2 is often effective to synthesize compounds which are difficult to synthesize according to Method 1. When $R_5$ represents an aryl group, it is possible to easily carry out ureidation upon the reaction with an amine. As a base which is employed on the step from compound (J) to compound (M) in Method 3, a metal hydride (such as lithium hydride, sodium hydride, potassium hydride, etc.), a metal alcoholate, a metal amide, etc. are suitably used. A base which does not have nucleophilicity, for example, sodium hydride, potassium tert-butoxide, or lithium diisopropylamide, etc. is preferred. The reduction step from compound (K) to compound (L) is carried out by reduction with a metal hydride or catalytic reduction.

Method 4 indicates a synthesis method of the coupler represented by formula (II). The coupler represented by formula (II) can be basically synthesized from the compound of formula (P) using the method as described in Japanese Patent Publication No. 30895/73. Compound (P) can be easily synthesized by diazotization of compound (M), followed by reduction.

Polymer couplers can be synthesized by solution polymerization and emulsion polymerization. With respect to the solution polymerization, the methods as described in U.S. Pat. No. 3,451,820 and Japanese Patent Application (OPI) No. 28745/83 can be utilized. More specifically, a monomer coupler containing a moiety represented by formula (I) or (II) and a non-color forming ethylenically unsaturated monomer as described above are dissolved in or mixed with a soluble organic solvent (for example, dioxane, methyl cellosolve, etc.) in an appropriate ratio, and polymerization is initiated at an appropriate temperature (in a range of from about 30° C. to 100° C.) with a free radical which is formed by a physical action such as irradiation of ultraviolet light, high energy radiations, etc. or a chemical action of an initiator such as a persulfate, hydrogen peroxide, benzoyl peroxide, azobisacrylonitrile, etc. The polymer thus-synthesized is isolated by extration with an organic solvent, concentration, or pouring into water after the completion of the polymerization reaction. With respect to emulsion polymerization, the method as described in U.S. Pat. No. 3,370,952 can be utilized.

General methods for introducing a group capable of being split off upon coupling into a coupler are described in the following.

(1) Method for connecting oxygen atom

A four-equivalent mother coupler according to the present invention is converted to a dye according to the method as described in Example 1 hereinafter. The resulting dye is hydrolyzed in the presence of an acid catalyst to form a ketone compound thereof. The ketone compound is hydrogenated with a Pd-carbon catalyst, or reduced with Zn-acetic acid or with sodium borohydride, to produce a 7-hydroxyl compound thereof. The resulting 7-hydroxyl compound is reacted with one of various kinds of halides to obtain the desired coupler which has an oxygen atom as the connecting atom to the coupling split-off group. For more detail, see U.S. Pat. No. 3,926,631 and Japanese Patent Application (OPI) No. 70817/82.

(2) Method for connecting nitrogen atom;

Methods for connecting a nitrogen atom are broadly classified into three groups. A method belonging to the first group comprises nitrosating the coupling active site of a coupler using an appropriate nitrosating agent, reducing the nitrosated compound by an appropriate method (for example, a hydrogenation method using Pd-carbon, etc., as a catalyst, a chemical reduction method using stannous chloride, etc., or so on) to convert a 7-amino compound thereof, and reacting the resulting 7-amino compound with one of various kinds of halides, as described in U.S. Pat. No. 3,419,391. According to this method, amide compounds can mainly be synthesized.

A method belonging to the second group comprises halogenating the 7-position of a coupler using an appropriate halogenating agent, for example, sulfuryl chloride, chlorine gas, bromine, N-chlorosuccinimide, N-bromosuccinimide, etc. as described in U.S. Pat. No. 3,725,067, and then replacing the resulting halogen atom by a nitrogen-containing hetero ring in the presence of an appropriate base catalyst, for example, triethylamine, sodium hydroxide, diazabicyclo-[2,2,2]-octane, anhydrous potassium carbonate, etc. to synthesize a coupler having a coupling split-off group connecting through a nitrogen atom at the 7-position thereof, as described in Japanese Patent Publication No. 45135/81. According to this method, couplers having a phenoxy group at the 7-position thereof which are compounds connecting through an oxygen atom can also be synthesized.

A method belonging to the third group is effective for the introduction of an aromatic nitrogen-containing hetero ring of a $6\pi$- or $10\pi$-electron system to the 7-position of a couper. This method comprises adding two or more moles of an aromatic nitrogen-containing heterocyclic compound of a $6\pi$- or $10\pi$-electron system to 1 mole of a 7-halogenated compound as prepared using the method described in the above second group and heating the resulting mixture at a temperature ranging from 50° C. to 150° C. in the absence of a solvent or at a temperature ranging from 30° C. to 150° C. in the presence of an aprotic polar solvent such as dimethylformamide, sulfolane, hexamethylphosphotriamide, etc. to introduce an aromatic nitrogen-containing heterocyclic group to the 7-position wherein the heterocyclic group is connected through the nitrogen atom, as described in Japanese Patent Publication No. 36577/82.

(3) Method for connecting sulfur atom

A coupler having an aromatic mercapto group or a heterocyclic mercapto group at the 7-position thereof can be synthesized using the method as described in U.S. Pat. No. 3,227,554. More specifically, an aryl mercaptan, a heterocyclic mercaptan, or a corresponding disulfide thereof is dissolved in a halogenated hydrocarbon type solvent, converted into a sulfenyl chloride using chlorine or sulfuryl chloride, and added to an aprotic solvent containing a four-equivalent mother coupler dissolved therein, whereby the desired compound can be synthesized. In order to introduce an alkylmercapto group into the 7-position, a method wherein a mercapto group is introduced into the coupling active site of a coupler and the mercapto group is reacted with a halide to synthesize a 7-alkylthio compound and a method wherein a 7-alkylthio compound is synthesized in one step using an S-(alkylthio)-isothiourea or a hydrochloride (or a hydrobromide), as described in U.S. Pat. No. 4,264,723, are useful.

Specific examples of the synthesis of the magenta couplers according to the present invention are set forth below.

SYNTHESIS EXAMPLE 1

Synthesis of Compound M-1:

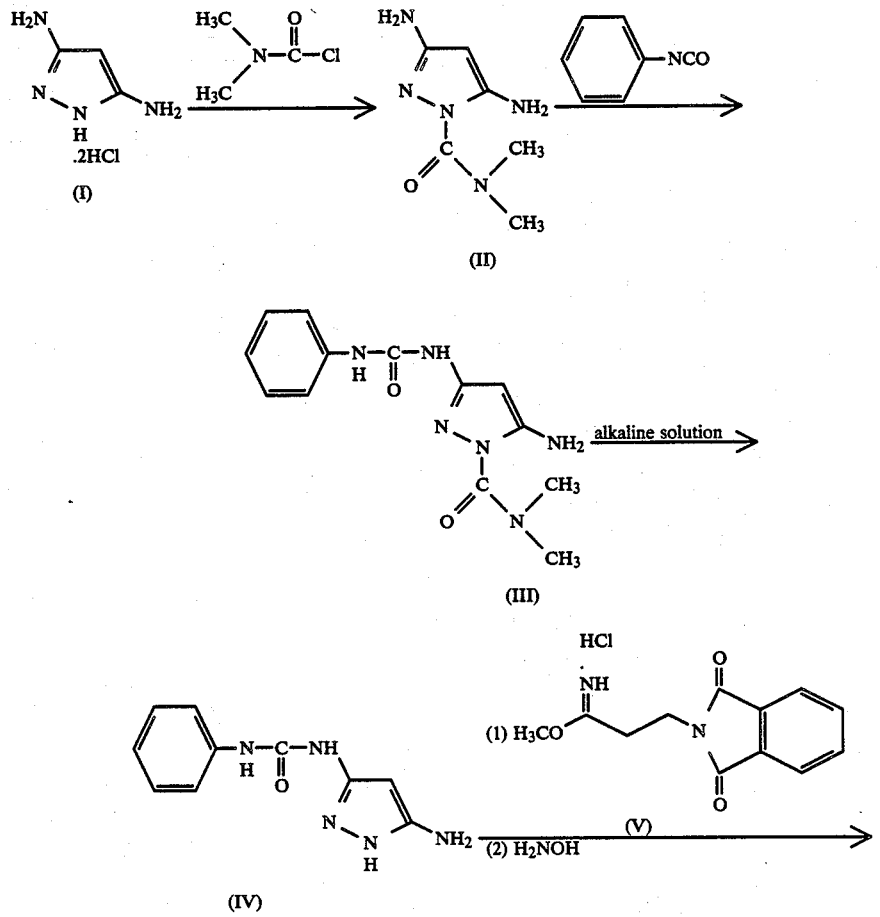

-continued

Synthesis of Compound M-1:

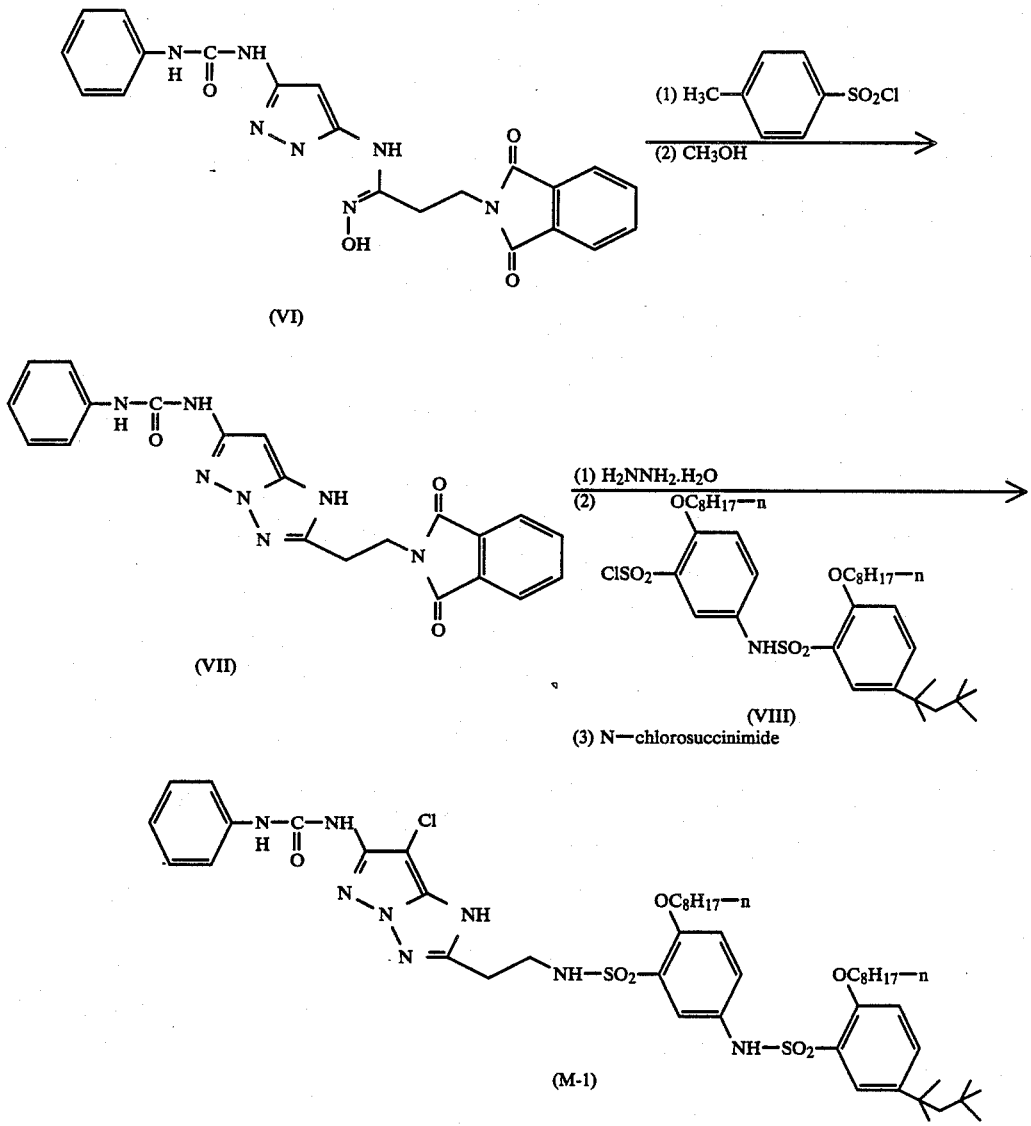

To 51 g (0.3 mol) of 3,5-diaminopyrazole dihydrochloride (Compound (I), which is a known compound obtained from malononitrile and hydrazine, was added 500 ml of acetonitrile and dissolved under reflux by heating. To the solution were added dropwise 83 ml (0.6 mol) of triethylamine, then 28 ml (0.3 mol) of N,N-dimethylcarbamoyl chloride, and thereafter 42 ml (0.3 mol) of triethylamine. After stirring under reflux by heating for 5 minutes, the reaction mixture was cooled with ice water, and the crystals thus-deposited were separated by filtration. The filtrate was concentrated and then purified by chromatography to obtain 34 g (0.2 mol, yield: 67%) of Compound (II).

NMR spectrum ($CDCl_3$): $\delta=5.2$ (2H, brs), 4.77 (1H, s), 3.8 (2H, brs), 3.07 (6H, s).

Melting point: 81° to 82° C.

10.1 g (0.06 mol) of Compound (II) was dissolved in 50 ml of acetonitrile, and to the solution was added dropwise 12 ml (0.11 mol) of phenyl isocyanate at room temperature. After stirring at room temperature for 30 minutes, the crystals thus-deposited were collected by filtration to obtain 11.2 g (0.039 mol, yield: 65%) of Compound (III).

Melting point: 172° to 173° C.

To 11.2 g (0.039 mol) of Compound (III) were added 500 ml of methanol and then 6.7 g (0.12 mol) of potassium hydroxide. After stirring under reflux by heating for 30 minutes, the methanol was distilled off. To the residue was added 100 ml of a saturated aqueous solution of sodium chloride, and the mixture was extracted with ethyl acetate. The ethyl acetate layer was dried over anhydrous sodium sulfate and then concentrated to obtain a crude product of Compound (IV) as an oil. NMR spectrum (DMSO-$d_6$): $\delta=8.8$–10.8 (2H, brs), 6.8–7.7 (5H, m), 5.27 (1H, s), 4.92 (2H, s).

22 g (0.1 mol) of Compound (IV) was dissolved in 80 ml of dimethyl sulfoxide, and to the solution was added 41 g (0.15 mol) of Compound (V) with stirring at room temperature and then further stirred at room temperature for 5 hours. Separately, 7.7 g (0.11 mol) of hydroxylamine hydrochloride was dissolved in 60 ml of methanol, and to the solution was added 22 ml of 28% methanol solution of sodium methoxide (0.11 mol) at 0° C. The resulting solution was added to the above-described dimethyl sulfoxide solution while removing the deposited sodium chloride by filtration. After stirring at room temperature for 1 hour, 500 ml of water was added to the reaction mixture, and a crude product of Compound (VI) was obtained as an oil by decantation.

To 43 g (0.1 mol) of Compound (VI) was added 200 ml of tetrahydrofuran, and the solution was stirred under cooling with ice. To the solution were added 19 g (0.1 mol) of p-toluenesulfonyl chloride and then dropwise 14 ml (0.1 mol) of triethylamine. After further stirring for 1 hour, the crystals thus-deposited were separated by filtration. To the filtrate was added 800 ml of methanol, the mixture was stirred under reflux by heating for 30 minutes and, then, the solvent was distilled off. To the resulting residue was added 100 ml of a saturated aqueous solution of sodium chloride and extracted with ethyl acetate. The ethyl acetate layer was dried over anhydrous sodium sulfate and then concentrated. The resulting residue was purified using chromatography to obtain 21 g (0.05 mol, yield: 51%) of Compound (VII).

To 21 g (0.05 mol) of Compound (VII) were added 210 ml of isopropyl alcohol and then dropwise 3.1 ml (0.05 mol) of hydrazine hydrate. The mixture was stirred under reflux by heating for 15 minutes and then, the solvent was distilled off. To the resulting residue was added 80 ml of N,N-dimethylacetamide, and the mixture was stirred under cooling with ice. To the mixture was added 35.0 (0.05 mol) of Compound (VIII) and then dropwise 6.9 ml (0.05 mol) of triethylamine. After further stirring for 10 minutes, 100 ml of a saturated aqueous solution of sodium chloride was added to the mixture, followed by extracting with ethyl acetate. The ethyl acetate layer was washed with water, dried with anhydrous sodium sulfate and then concentrated. The resulting residue was purified using chromatography and the oil thus-obtained was dissolved in 500 ml of chloroform. To the solution was added 4.0 g (0.03 mol) of N-chlorosuccinimide with stirring at room temperature. After stirring for 10 minutes, the mixture was washed with water, dried, and concentrated. The resulting residue was purified by chromatography to obtain 27.5 g (0.028 mol, yield: 56%) of Compound M-1.

SYNTHESIS EXAMPLE 2

Synthesis of Compound M-2:

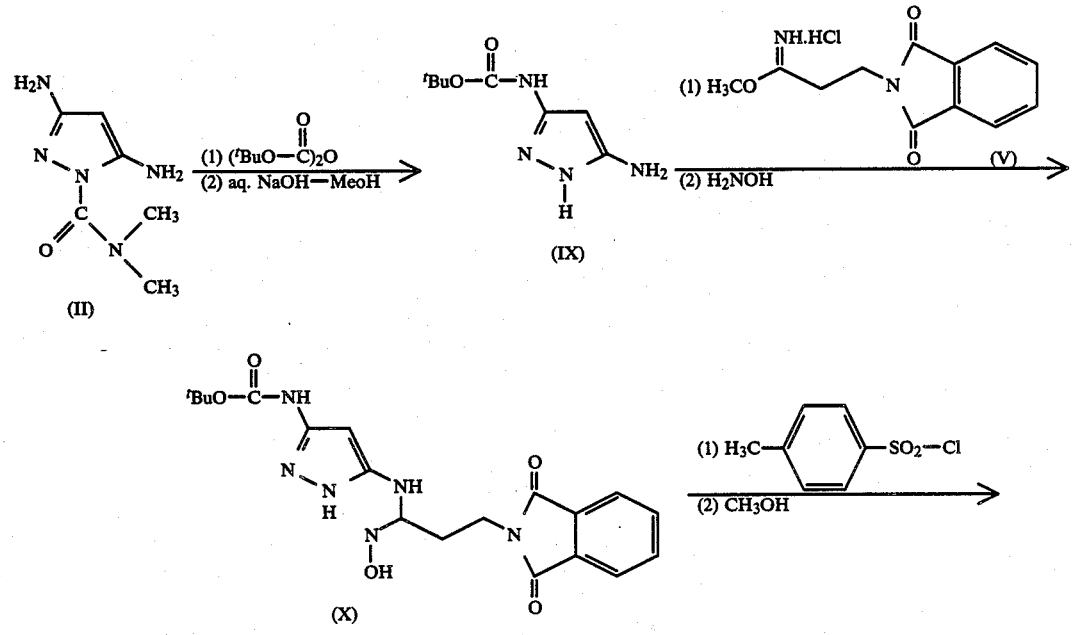

-continued

Synthesis of Compound M-2:

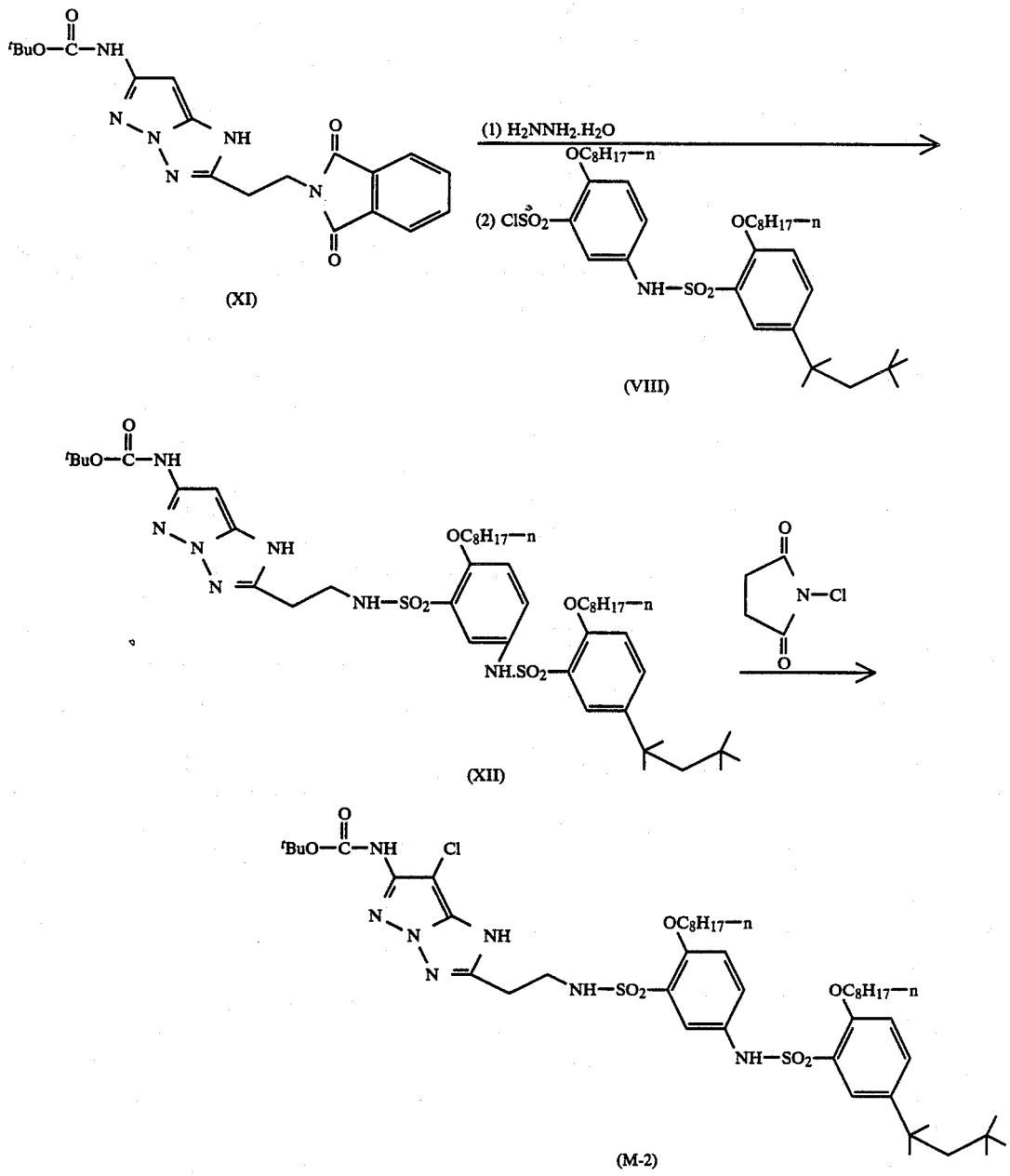

55 g (0.33 mol) of Compound (II) was dissolved in 1 l of tetrahydrofuran, 142 g (0.66 mol) of di-tertbutyl bicarbonate was added thereto, and the mixture was stirred under reflux by heating for 18 hours. After distilling off the solvent, the resulting residue was purified by chromatography to obtain 58.1 g (0.22 mol, yield: 66%) of crystals.

NMR spectrum (DMSO-$d_6$): $\delta$=9.3 (1H, brs), 5.9 (2H, brs), 5.57 (1H, s), 3.07 (6H, s), 1.45 (9H, s).

To the crystals were added 1 l of methanol and then dropwise 200 ml of a 2N aqueous solution of sodium hydroxide, and the mixture was stirred under reflux by heating for 1 hour. The mixture was then neutralized with ice, the solvent was distilled off, and the salt was separated by filtratin, whereby 47 g of a crude product of Compound (IX) was obtained as an oil.

40 g (2.0 mol) of Compound (IX) was dissolved in 100 ml of methanol, 54 g (0.2 mol) of Compound (V) was added thereto at room temperature, and the mixture was stirred for 3 hours. Separately, 14 g (0.2 mol) of hydroxylamine hydrochloride was dissolved in 110 ml of methanol, and to the solution was added 40 ml of a 28% methanol solution of sodium methoxide (0.2 mol) at 0° C. The resulting solution was added to the above-described reaction solution of Compound (IX) and Compound (V) while removing the deposited sodium chloride by filtration. After stirring at room temperature for 3 hours, the crystals thus-deposited were collected by filtration to obtain 36 g (0.88 mol, yield: 44%) of Compound (X).

Melting point: 176° to 177° C.

To 39 g (0.094 mol) of Compound (X) were added 40 ml of N,N-dimethylacetamide and 80 ml of tetrahydrofuran. To the solution were added 18 g (0.094 mol) of p-toluenesulfonyl chloride and then dropwise 13 ml of triethylamine while cooling with ice. After stirring for 1 hour, the mixture was poured into 500 ml of ice water, and the crystals thus-deposited were collected by filtration.

Melting point: 102° to 103° C.

The crystals were dissolved in 1 l of methanol, the solution was stirred under reflux by heating for 30 minutes and, then, 500 ml of the methanol was distilled off. To the residue was added 100 ml of cold water, and the crystals thus-deposted were collected by filtration to obtain 25 g (0.063 mol, yield: 67%) of Compound (XI).

Melting point: 175° C. (decomposed).

NMR spectrum (DMSO-$d_6$): $\delta$=12.4 (1H, s), 9.3 (1H, s), 7.8 (4H, s), 5.7 (1H, s), 3.9 (2H, t), 3.0 (2H, t), 1.4 (9H, s)

To 25 g (0.063 mol) of Compound (XI) were added 200 ml of isopropyl and then dropwise 3.9 ml (0.063 mol) of hydrazine hydrate. The mixture was stirred under reflux by heating for 2 hours and, then, the solvent was distilled off. To the resulting residue was added 100 ml of N,N-dimethylacetamide. To the mixture were added 44 g (0.063 mol) of Compound (VIII) and then dropwise 8.7 ml (0.063 mol) of triethyamine under cooling with ice. After stirring for 30 minutes, 100 ml of a saturated aqueous solution of sodium chloride was added to the mixture, followed by extraction with ethyl acetate. The ethyl acetate layer was washed with water, dried over anhydrous sodium sulfate, and then concentrated. The resulting residue was purified by column chromatography to obtain 26 g (0.028 mol, yield: 44%) of Compound (XII).

26 g (0.028 mol) of Compound (XII) was dissolved in 500 ml of chloroform, and 3.7 g (0.028 mol) of N-chlorosuccinimide was added thereto at room temperature. After stirring for 10 minutes, the mixture was washed with water and dried over anhydrous sodium sulfate, and the solvent was distilled off. The resulting residue was purified by column chromatography to obtain 27 g (0.028 mol, yield: 100%) of Compound M-2.

SYNTHESIS EXAMPLE 3

Synthesis of Compound M-3:

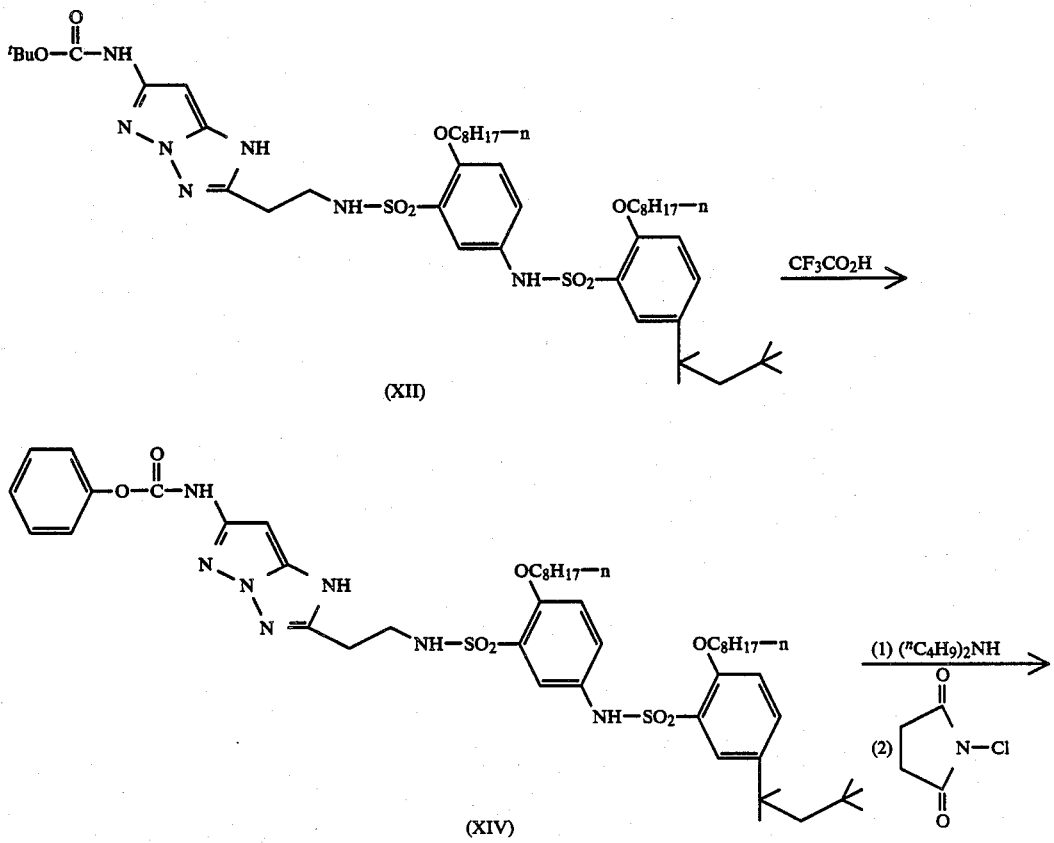

-continued

Synthesis of Compound M-3:

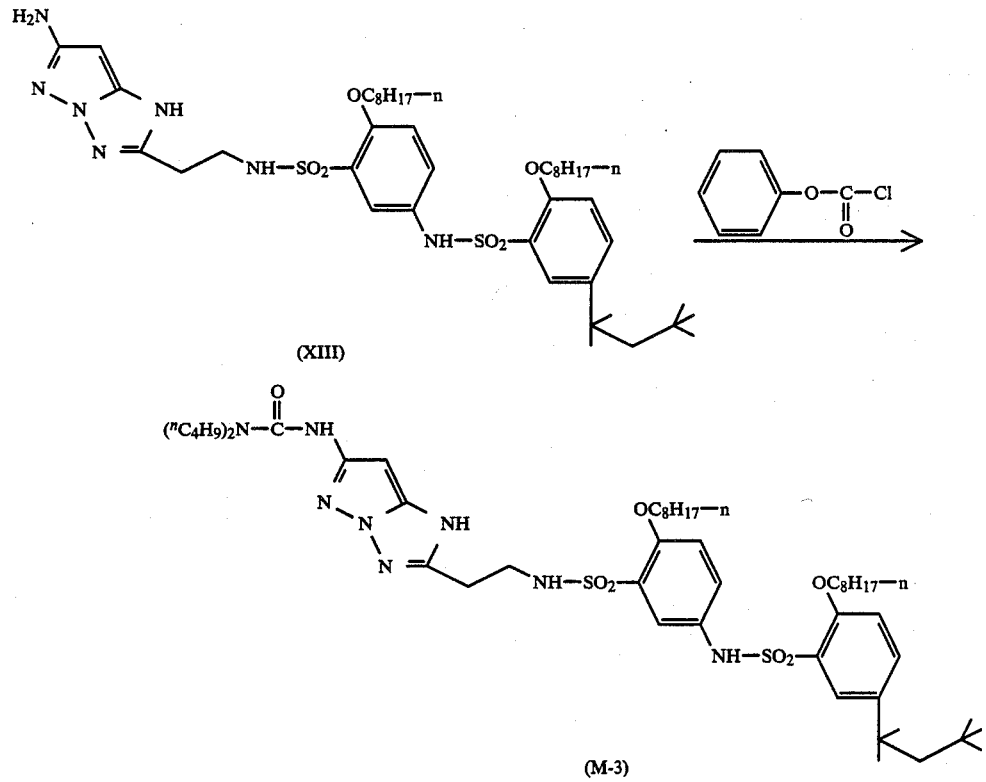

13.0 g (14 mmol) of Compound (XII) was dissolved in 26 ml of trifluoroacetic acid, and the solution was stirred at room temperature for 30 minutes. To the mixture was added 100 ml of ethyl acetate, washed with water, dried over anhydrous sodium sulfate, and concentrated. The resulting residue was purified by chromatography to obtain 10.6 g (12.8 mmol, yield: 91%) of Compound (XIII).

10.6 g (12.8 mmol) of Compound (XIII) was dissolved in 50 ml of acetonitrile, and to the solution was added 3.5 ml (25.6 mmol) of triethyalmine and then 4.0 g (25.6 mmol) of phenyl chloroformate under cooling with ice. The mixture was stirred at room temperature for 1 hour, 100 ml of ethyl acetate was added thereto, and the mixture was washed with water, dried over anhydrous sodium sulfate, and concentrated. The resulting residue was purified by chromatography to obtain 10.3 g (9.6 mmol, yield: 75%) of Compound (XIV).

10.3 g (9.6 mmol) of Compound (XIV) was dissolved in 100 ml of chloroform, and to the solution was added dropwise 2.6 g (20 mmol) of di-n-butylamine at room temperature. After stirring for 1 hour, 100 ml of ethyl acetate was added thereto, and the mixture was washed with water, dried over anhydrous sodium sulfate, and concentrated. The resulting residue was dissolved in 200 ml of chloroform, and to the solution was added 1.06 g (7.9 mmol) of N-chlorosuccinimide at room temperature. After stirring for 10 minutes, the mixture was washed with water, dried over anhydrous sodium sulfate, and concentrated. The resulting residue was purified by chromatography to obtain 7.8 g (7.6 mmol, yield: 81%) of Compound M-3.

The light-fastness of the magenta color image formed from the magenta coupler according to the present invention can be improved by using such together with a color image stabilizing agent represented by the following formula:

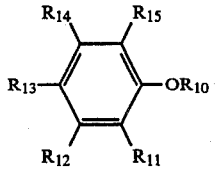

wherein $R_{10}$ represents a hydrogen atom, an alkyl group, an aryl group, or a heterocyclic group; $R_{11}$, $R_{12}$, $R_{14}$, and $R_{15}$ each represents a hydrogen atom, a hydroxyl group, an alkyl group, an aryl group, an alkoxy group, or an acylamino group; $R_{13}$ represents an alkyl group, a hydroxyl group, an aryl group, or an alkoxy group; $R_{10}$ and $R_{11}$ may be combined with each other to form a 5-membered or 6-membered ring and in such a case, $R_{12}$ represents a hydroxyl group or an alkoxy group; $R_{10}$ and $R_{11}$ may be combined with each other to form a methylenedioxy ring; and $R_{13}$ and $R_{14}$ may be combined with each other to form a 5-membered hydrocarbon ring and in such a case, $R_{10}$ represents an alkyl group, an aryl group, or a heterocyclic group.

The color image stabilizing agent can also include those described in U.S. Pat. Nos. 3,935,016, 3,982,944, 4,254,216, 3,764,337, 3,432,300, 3,574,627, 3,573,050, and 3,700,455, Japanese Patent Application (OPI) Nos. 21004/80, 145530/79, 152225/77, 20327/78, 17729/78, and 6321/80, British Patent Application (OPI) Nos. 2,077,455, 2,062,888, and 1,347,556, Japanese Patent Publication Nos. 12337/79, 31625/73, etc.

The coupler according to the present invention can be employed by incorporating into a photographic light-sensitive material or by adding to a color developing solution. In case of incorporating the coupler into a photographic light-sensitive material, a suitable amount thereof ranges from $2\times10^{-3}$ to $5\times10^{-1}$ mol, preferably from $1\times10^{-2}$ to $5\times10^{-1}$ mol, per mol of silver halide. When a polymer coupler is used, the amount of the polymer coupler added is adjusted so that the amount of the color forming portion thereof is within the above-described range. On the other hand, when the coupler is added to a color developing solution, it is used in an amount of from 0.001 to 0.1 mol, preferably from 0.01 to 0.05 mol, per 1,000 ml of the solution.

A preferred embodiment of the present invention is a silver halide color photographic material containing the coupler according to the present invention.

The pyrazoloazole type coupler used in the present invention can be incorporated into photographic light-sensitive materials using various known dispersing methods. Typical examples thereof include a solid dispersing method and an alkali dispersing method, preferably a latex dispersing method, and more preferably an oil droplet-in-water type dispersing method. By means of the oil droplet-in-water type dispersing method, couplers are dissolved in either an organic solvent having a high boiling point of 175° C. or more, an auxiliary solvent having a low boiling point, or a mixture thereof and, then, the solution is finely dispersed in an aqueous medium such as water or an aqueous gelatin solution, etc. in the presence of a surface active agent. Specific examples of the organic solvents having a high boiling point are those as described in U.S. Pat. No. 2,322,027, etc. The dispersion may involve a phase inversion, and the auxiliary solvent may be removed or reduced, if desired, by distillation, noodle washing, or ultrafiltration before coating on a support.

Specific examples of the organic solvent having a high boiling point include phthalic acid esters (e.g., dibutyl phthalate, dicyclohexyl phthalate, di-2-ethylhexyl phthalate, didodecyl phthalate, etc.), phosphoric or phosphonic acid esters (e.g., triphenyl phosphate, tricresyl phosphate, 2-ethylhexyldiphenyl phosphate, tricyclohexyl phosphate, tri-2-ethylhexyl phosphate, tridodecyl phosphate, tributoxyethyl phosphate, trichloropropyl phosphate, di-2-ethylhexylphenyl phosphate, etc.), benzoic acid esters (e.g., 2-ethylhexyl benzoate, dodecyl benzoate, 2-ethylhexyl-p-hydroxybenzoate, etc.), amides (e.g., diethyldodecanamide, N-tetradecylpyrrolidone, etc.), alcohols or phenols (e.g., isostearyl alcohol, 2,4-di-tert-amylphenol, etc.), aliphatic carboxylic acid esters (e.g., dioctyl azelate, glycerol tributylate, isostearyl lactate, trioctyl citrate, etc.), aniline derivatives (e.g., N,N-dibutyl-2-butoxy-5-tert-octylaniline, etc.), and hydrocarbons (e.g., paraffins, dodecylbenzene, diisopropyl naphthalene, etc.). Suitable auxiliary solvents include organic solvents having a boiling point of about 30° C. or more, preferably from about 50° C. to about 160° C. Typical examples thereof include ethyl acetate, butyl acetate, ethyl propionate, methyl ethyl ketone, cyclohexanone, 2-ethoxyethyl acetate, and dimethylformamide.

The processes and advantages of latex dispersing methods and the specific examples of latexes for loading are described in U.S. Pat. No. 4,199,363, West German Patent Application (OLS) Nos. 2,541,274, 2,541,230, etc.

Typical examples of silver halide used in the silver halide emulsion according to the present invention include mixed silver halides, for example, silver chlorobromide, silver chloroiodobromide, and silver iodobromide, etc., as well as silver chloride and silver bromide. When the present invention is applied to color papers or color reversal papers, silver halides which are preferably used are silver chlorobromide which does not substantially contain silver iodide. The term "silver halide does not substantially contain silver iodide" means that the silver halide has a silver iodide content of 2 mol % or less and preferably 1 mol % or less and, most preferably, the silver halide does not contain silver iodide at all.

When the color forming property is high and the formation of fog is apt to occur in the present invention, it is preferred that the silver chloride content is 30 mol % or less, particularly 20 mol % or less. On the other hand, in case of contemplating a rapid processing utilizing high color forming property, preferred results can sometimes be obtained when the silver chloride content is 80 mol % or more, particularly 90 mol % or more.

Silver halide grains may have different layers in the inner portion and the surface portion, multiphase structures containing junctions or may be uniform throughout the grains. Further, a mixture of these silver halide grains having different structures may be employed.

The average grain size of silver halide grains used in the present invention (the grain size being defined as grain diameter if the grain has a spherical or nearly spherical form and as a length of the edge if the grain has a cubic form, and being averaged based on projected areas of the grains) is preferably from 0.1 μm to 2 μm and particularly from 0.15 μm to 1 μm.

A so-called monodisperse silver halide emulsion having a narrow grain size distribution can be employed in the present invention. The monodisperse silver halide emulsion is a silver halide emulsion in which at least 90% and particularly at least 95% by number or by weight of the total silver halide grains have a size within the range of ±40% of the average grain size. Further, in order to achieve the desired gradation of the photographic light-sensitive material, two or more monodisperse silver halide emulsions which have different grain sizes from each other can be mixed in one emulsion layer or can be coated in the form of superimposed layers which have substantially the same spectral sensitivity. Moreover, two or more polydisperse silver halide emulsions or combinations of a monodisperse emulsion and a polydisperse emulsion may be employed in a mixture or in the form of superimposed layers.

Silver halide grains which can be used in the present invention may have a regular crystal structure, for example, a cubic, octahedral, dodecahedral, or tetradecahedral structure, etc., an irregular crystal structure, for example, a spherical structure, etc., or a composite structure thereof. Further, tabular silver halide grains can be used. Particularly, a silver halide emulsion wherein tabular silver halide grains having a ratio of diameter/thickness of 5/1 or more, preferably 8/1 or more are account for at least 50% of the total projected area of the silver halide grains present can be employed. In addition, mixtures of silver halide grains having different crystal structures may be used. These silver halide emulsions may be those of surface latent image type in which latent images are formed mainly on the surface thereof or those of internal latent image type in which latent images are formed mainly in the interior thereof.

Photographic emulsions as used in the present invention can be prepared in any suitable manner, for example, by the methods as described in P. Glafkides, *Chimie et Photographique,* Paul Montel (1967), G. F. Duffin, *Photographic Emulsion Chemistry,* The Focal Press (1966), and V. L. Zelikman et al., *Making and Coating Photographic Emulsion,* The Focal Press (1964). That is, any of an acid process, a neutral process, an ammonia process, etc., can be employed.

Soluble silver salts and soluble halogen salts can be reacted by techniques such as a single jet process, a double jet process, and a combination thereof. In addition, there can be employed a method (so-called reversal mixing process) in which silver halide grains are formed in the presence of an excess of silver ions. As one system of the double jet process, a so-called controlled double jet process in which the pAg in a liquid phase where a silver halide is formed is maintained at a predetermined level can be employed. This process can prepare a silver halide emulsion in which the crystal form is regular and the particle size is nearly uniform.

During the step of formation or physical ripening of silver halide grains, cadmium salts, zinc salts, lead salts, thallium salts, iridium salts or complex salts thereof, rhodium salts or complex salts thereof, iron salts or complex salts thereof, etc. may be allowed to coexist.

The photographic emulsions used in the present invention are usually conducted with physical ripening, chemical ripening, and spectral sensitization. Various kins of additives which can be employed in these steps are described in *Research Disclosure,* No. 17643 (December, 1978) and Ibid., No. 18716 (November, 1979), and concerned items thereof are summarized in the table shown below.

Further, known photographic additives which can be used in the present invention are also described in the above-mentioned *Research Disclosure* references, and concerned items thereof are summaried in the table below.

| Kind of Additives | Research Disclosure No. 17643 | Research Disclosure No. 18716 |
|---|---|---|
| 1. Chemical Sensitizers | p. 23 | p. 648, right column |
| 2. Sensitivity Increasing Agents | | p. 648, right column |
| 3. Spectral Sensitizers and Supersensitizers | pp. 23–24 | p. 648, right column to p. 649, right column |
| 4. Whitening Agents | p. 24 | — |
| 5. Antifoggants and Stabilizers | pp. 24–25 | p. 649, right column |
| 6. Light-Absorbers, Filter Dyes and Ultraviolet Light Absorbents | pp. 25–26 | p. 649, right column to p. 650, left column |
| 7. Antistaining Agents | p. 25, right column | p. 650, left column to right column |
| 8. Dye Image Stabilizers | p. 25 | — |
| 9. Hardeners | p. 26 | p. 651, left column |
| 10. Binders | p. 26 | p. 651, left column |
| 11. Plasticizers and Lubricants | p. 27 | p. 650, right column |
| 12. Coating Aids and Surfactants | pp. 26–27 | p. 650, right column |
| 13. Antistatic Agents | p. 27 | p. 650, right column |

In the present invention, various color couplers can be employed, and specific examples thereof are described in the patents cited in *Research Disclosure,* No. 17643, "VII-C" to "VII-G" described above. As dye forming couplers, couplers capable of providing three primary colors (i.e., yellow, magenta, and cyan) in the substractive process upon color development are important. Specific examples of preferred diffusion-resistant, four-equivalent or two-equivalent couplers are described in the patents cited in *Research Disclosure,* No. 17643, "VII-C" and "VII-D" as mentioned above. In addition, couplers as described below are preferably employed in the present invention.

As typical yellow couplers used in the present invention, hydrophobic acylacetamide type couplers having a ballast group are exemplified. Specific examples thereof are described in U.S. Pat. Nos. 2,407,210, 2,875,027, 3,265,506, etc. In the present invention two-equivalent yellow couplers are preferably employed.

Typical examples of two-equivalent yellow couplers include yellow couplers of the oxygen atom-releasing type as described in U.S. Pat. Nos. 3,408,194, 3,447,928, 3,033,501, 4,022,620, etc. and yellow couplers of the nitrogen atom-releasing type as described in Japanese Patent Publication No. 10739/83, U.S. Pat. Nos. 4,401,752 and 4,326,024, *Research Disclosure,* No. 18053 (April, 1979), British Pat. No. 1,425,020, West German Patent Application (OLS) Nos. 2,219,917, 2,261,361, 2,329,587, 2,433,812, etc. α-Pivaloylacetanilide type couplers are characterized by fastness, partiularly lightfastness, of dyes formed, and α-benzoylacetanilide type couplers are characterized by providing high color density.

As magenta couplers which can be used in combination with the pyrazoloazole type magenta coupler according to the present invention, hydrophobic indazolone type couplers, cyanoacetyl type couplers, and preferably 5-pyrazolone type couplers, and pyrazoloazole type couplers other than those according to the present invention, each having a ballast group, are exemplified. Of the 5-pyrazolone type couplers, those substituted with an arylamino group or an acylamino group at the 3-position thereof are preferred in view of the hue of the dyes formed therefrom and the color density. Typical examples thereof are described in U.S. Pat. Nos. 2,311,082, 2,343,703, 2,600,788, 2,908,573, 3,062,653, 3,152,896, 3,936,015, etc. As split-off groups for two-equivalent 5-pyrazolone type couplers, nitrogen atom-releasing groups as described in U.S. Pat. No. 4,310,619 and arylthio groups as described in U.S. Pat. No. 4,351,897 are particularly preferred. Further, 5-pyrazolone type couplers having a ballast group as described in European Pat. No. 73,636 are advantageous because they provide high color density.

As cyan couplers used in the present invention, hydrophobic and diffusion-resistant naphthol type and phenol type couplers are exemplified. Typical examples thereof include naphthol type couplers as described in U.S. Pat. No. 2,474,293 and preferably oxygen atom-releasing type two-equivalent naphthol type couplers as described in U.S. Pat. Nos. 4,052,212, 4,146,396, 4,228,233, 4,296,200, etc. Specific examples of phenol type couplers are those as described in U.S. Pat. Nos. 2,369,929, 2,801,171, 2,772,162, 2,895,826, etc.

Cyan couplers which are fast to humidity and temperature are preferably used in the present invention. Typical examples thereof include phenol type cyan couplers having an alkyl group more than a methyl group at the meta-position of the phenol nucleus as described in U.S. Pat. No. 3,772,002, 2,5-diacylamino-substituted phenol type couplers as described in U.S. Pat. Nos. 2,772,162, 3,758,308, 4,126,396, 4,334,011, and 4,327,173, West German Patent Application (OLS) No. 3,329,729, European Pat. No. 121,365, etc., phenol type couplers having a phenylureido group at the 2-position thereof and an acylamino group at the 5-position thereof as described in U.S. Pat. Nos. 3,446,622, 4,333,999, 4,451,559, 4,427,767, etc.

Further, couplers capable of forming appropriately diffusible dyes can be used together in order to improve graininess. Specific examples of such types of magenta couplers are described in U.S. Pat. No. 4,366,237, British Pat. No. 2,125,570, etc. and those of yellow, magenta and cyan couplers are described in European Pat. No. 96,570, West German Patent Application (OLS) No. 3,234,533, etc.

Dye-forming couplers and the above-described special couplers may form polymers including dimers or more. Typical examples of polymerized dye-forming couplers are described in U.S. Pat. Nos. 3,451,820, 4,080,211, etc. Specific examples of polymerized magenta couplers are described in British Pat. No. 2,102,173, U.S. Pat. No. 4,367,282, etc.

Couplers capable of releasing a photographically useful residue during the course of coupling can be also employed preferably. Specific examples of useful DIR couplers capable of releasing a development inhibitor are described in the patents cited in *Research Disclosure,* No. 17643, "VII-F" described above.

The color photographic light-sensitive material according to the present invention can be subjected to development processing in a conventional manner as described in *Research Disclosure,* No. 17643, pages 28 to 29 and Ibid., No. 18716, pages 651, left column to right column.

After a development, bleach-fixing, or fixing step, the color photographic light-sensitive material according to the present invention is usually subjected to a water-washing step or a stabilizing step.

The processing steps (image forming steps) which are applied to the present invention are described in detail below.

In the present invention, the processing time for the color development step is preferably not more than 2 minutes and 30 seconds, more preferably from 30 seconds to 1 minute. The term "processing time for the color development step" as used herein means the period of time from the time when the photographic light-sensitive material comes into contact with the color developing solution to the time when the photographic material comes into contact with the subsequent processing solution and, therefore, it includes a transfer time between the processing baths.

The color developing solution which can be used in development processing according to the present invention is an alkaline aqueous solution containing preferably an aromatic primary amine type color developing agent as a main component. As the color developing agent, a p-phenylenediamine type compound is preferably employed. Typical examples of the p-phenylenediamine type compounds include 3-methyl-4-amino-N,N-diethylaniline, 3-methyl-4-amino-N-ethyl-N-β-methanesulfonamidoethylaniline, 3-methyl-4-amino-N-ethyl-N-β-methoxyethylaniline, or a sulfate, hydrochloride, phosphate, p-toluenesulfonate, tetraphenylborate, or p-(tert-octyl)-benzenesulfonate thereof, etc.

Aminophenol type derivatives which can be used include, for example, o-aminophenol, p-aminophenol, 4-amino-2-methylphenol, 2-amino-3-methylphenol, 2-oxy-3-amino-1,4-dimethylbenzene, etc.

In addition, the compounds as described in L. F. A. Mason, *Photographic Processing Chemistry,* The Focal Press, pages 226 to 229 (1966), U.S. Pat. Nos. 2,193,015 and 2,592,364, Japansese Patent Application (OPI) No. 64933/73, etc. may be used.

Two or more kinds of color developing agents may be employed in combination, if desired.

The processing temperature with the color developing solution used in the present invention is preferably from 30° C. to 50° C., more preferably from 33° C. to 45° C.

It is preferred that the color developing solution used in the present invention does not substantially contain benzyl alcohol as a development accelerator. The term "color development solution does not substantially contain benzyl alcohol" means that the color developing solution preferably contains benzyl alcohol in an amount of not more than 2 mol, more preferably not more than 0.5 ml, per liter of the solution. It is most preferred that the color developing solution does not contain benzyl alcohol at all.

The color developing solution used in the present invention may contain an appropriate development accelerator other than benzyl alcohol. Examples of such development accelerators include various pyridinium compounds and other cationic compounds as described, for example, in U.S. Pat. Nos. 2,648,604 and 3,171,248, and Japanese Patent Publication No. 9503/69; cationic dyes such as phenosafranine; neutral salts such as thallium nitrate or potassium nitrate; polyethylene glycol and derivatives thereof as described in Japanese Patent Publication No. 9304/69 and U.S. Pat. Nos. 2,533,990, 2,531,832, 2,950,970, and 2,577,127; nonionic compounds such as polythioethers; and thioether type compounds such as those described in U.S. Pat. No. 3,201,242; compounds as described in U.S. Pat. No. 3,201,242; compounds as described in Japanese Patent Application (OPI) Nos. 156934/83, 220344/85, etc.

In development processing using a short period of processing time, not only a means for accelerating development but also a technique for preventing development fog are important. As suitable antifoggants, alkali metal halides such as potassium bromide, sodium bromide, or potassium iodide, and organic antifoggants are preferred. Examples of organic antifoggants include nitrogen-containing heterocyclic compounds such as benzotriazole, 6-nitrobenzimidazole, 5-nitroisoindazole, 5-methylbenzotriazole, 5-nitrobenzotriazole, 5-chlorobenzotriazole, 2-thiazolylbenzimidazole, 2-thiazolylmethylbenzimidazole, or hydroxyazaindolizine; mercapto-substituted heterocyclic compounds such as 1-phenyl-5-mercaptotetrazole, 2-mercaptobenzimidazole, or 2-mercaptobenzothiazole; and mercapto-substituted aromatic compounds such as thiosalicyclic acid. Of these compounds, halides are particularly preferred. These antifoggants may be dissolved from color photographic light-sensitive materials in a color developing solution during processing and accumulated in the color developing solution.

The color developing solution used in the present invention can further contain pH buffering agents, such as carbonates, borates, or phosphates of alkali metals, etc.; preservatives such as hyroxylamine, triethanolamine, the compounds as described in West German Patent Application (OLS) No. 2,622,950, sulfites, bisulfites, etc.; organic solvents such as diethylene glycol, etc.; dye-forming couplers; competing couplers; nucleating agents such as sodium borohydride, etc.; auxiliary developing agents such as 1-phenyl-3-pyrazolidone, etc.; viscosity imparting agents; and chelating agents including aminopolycarboxylic acids as represented by ethylenediaminetetraacetic acid, nitrilotriacetic acid, cyclohexanediaminetetraacetic acid, iminodiacetic acid, N-hydroxymethylethylenediaminetriacetic acid, diethylenetriaminepentaacetic acid, triethylenetetraminehexaacetic acid, the compounds as described in Japanese Patent Application (OPI) No. 195845/83, etc., organic phosphonic acids such as 1-hydroxyethylidene-1,1'-diphosphonic acid, those as described in *Research Disclosure,* No. 18170 (May, 1979), etc., aminophosphonic acids such as aminotris(methylenephosphonic acid), ethylenediamine-N,N,N',N'-tetramethylenephosphonic acid, etc., phosphonocarboxylic acids as described in Japanese Patent Application (OPI) Nos. 102726/77, 42730/78, 121127/79, 4024/80, 4025/80, 126241/80, 65955/80, and 65956/80, *Research Disclosure,* No. 18170 (May, 1979), etc.

Furthermore, the color development bath can be divided into two or more baths, if desired, and a replenisher for the color developing solution may be supplied from the first bath or the last bath in order to conduct shortening the developing time or reduction of the amount of the replenisher.

After color development, the silver halide color photographic material is usually subjected to a bleach processing. The bleach processing may be performed simultaneously with a fixing processing (bleach-fixing), or they may be performed independently.

Bleaching agents which can be used include compounds of polyvalent metals, for example, iron (III), cobalt (III), chromium (VI), and copper (II), peracids, quinones, and nitroso compounds. For example, ferricyanides; dichromates; organic complex salts of iron (III) or cobalt (III), for example, complex salts of aminopolycarboxylic acids (e.g., ethylenediaminetetraacetic acid, diethylenetriaminepentaacetic acid, nitrilotriacetic acid, 1,3-diamino-2-propanoltetraacetic acid, etc.) or organic acids (e.g., citric acid, tartaric acid, malic acid, etc.); persulfates; permanganates; nitrosophenol, etc. can be used. Of these compounds, potassium ferricyanide, sodium iron (III) ethylenediaminetetraacetate, ammonium iron (III) ethylenediaminetetracetate, ammonium iron (III) ethylenediaminetetraacetate, ammonium iron (III) triethylenetetraminepentaacetate, and a persulfate are particularly preferred. Further, ethylenediaminetetraacetic acid iron (III) complex salts are useful in both an independent bleaching solution and a mono-bath bleach-fixing solution.

In the bleaching solution or the bleach-fixing solution, various kinds of accelerators may be employed together, if desired. Examples thereof used include bromine ions, iodine ions, thiourea type compounds as described in U.S. Pat. No. 3,706,561, Japanese Patent Publication Nos. 8506/70 and 26586/74, Japanese Patent Application (OPI) Nos. 32735/78, 36233/78, 37016/78, etc., thiol type compounds as described in Japanese Patent Application (OPI) Nos. 124424/78, 95631/78, 57831/78, 32736/78, 65732/78, and 52534/79, U.S. Pat. No. 3,893,858, etc., heterocyclic compounds as described in Japanese Patent Application (OPI) Nos. 59644/74, 140129/75, 28426/78, 141623/78, 104232/78, 35727/79, etc., thioether type compounds as described in Japanese Patent Application (OPI) Nos. 20832/77, 25064/80, 26506/80, etc., quaternary amines as described in Japanese Patent Application (OPI) No. 84440/73, etc., thiocarbamoyls as described in Japanese Patent Application (OPI) No. 42349/74, etc. or the like.

As fixing agents which can be used in a bleach-fixing solution or a fixing solution, thiosulfates, thiocyanates, thioether type compounds, thioureas, a large amount of iodides, etc. are suitable. Thiosulfates can generally be employed. In the bleach-fixng solution or the fixing solution, sulfites, bisulfites, or carbonylbisulfite adducts are preferably employed as preservatives.

After the bleach-fixing processing or the fixing processing, water-washing processing is usually carried out. In the water-washing step, various known compounds may be employed for the purpose of preventing precipitation or saving water, etc. For example, a water softener such as an inorganic phosphoric acid, an aminopolycarboxylic acid, or an organic phosphoric acid, etc. for preventing the formation of precipitates; a sterilizer or antimold for preventing the propagation of various bacteria, algae, and molds; a hardener such as a magnesium salt or an aluminum salt, etc.; or a surface active agent for reducing drying load or preventing drying marks, or the like may be added, if desired. Further, the compounds as described in L. E. West, *Photo. Sci. and Eng.,* Vol. 9, No. 6 (1965) may be added. Particularly, the addition of chelating agents and antimolds is effective.

The water-washing step is ordinarily carried out using a countercurrent water-washing processing with two or more tanks in order to save water. Further, in place of the water-washing step, a multistage countercurrent stabilizing processing step as described in Japanese Patent Application (OPI) No. 8543/82 may be conducted. In this step, two to nine tanks of countercurrent bath is required. To the stabilizing bath, various kinds of compounds are added for the purpose of stabilizing images formed. Representative examples of the additives include various buffers (for example, borates, metaborates, borax, phosphates, carbonates, potassium hydroxide, sodium hydroxide, aqueous ammonia, monocarboxylic acids, dicarboxylic acids, polycarboxylic acids, etc. being used in combination) for the purpose of adjusting the pH of layers (for example, pH of 3 to 8), and formalin, etc. In addition, various additives, for example, water softeners (for example, inorganic phosphoric acids, aminopolycarboxylic acids, organic phosphric acids, aminopolyphosphonic acids, phosphonocarboxylic acids, etc.), sterilizers (for example, benzoisothiazolinones, isothiazolones, 4-thiazolinebenzimidazoles, halogenated phenols, etc.), surface active agents, fluorescent whitening agents, hardeners, etc. may be employed, if desired. Two or more compounds for the same or different purposes may be employed together.

Further, it is preferred to add various ammonium salts such as ammonium chloride, ammonium nitrate, ammonium sulfate, ammonium phosphate, ammonium sulfite, ammonium thiosulfate, etc., as a pH adjusting agent for layers after processing.

The present invention can be applied to various kinds of color photographic light-sensitive materials. Representative examples thereof include color negative films for general use or cinematography, color reversal films for slides or television, color papers, color positive films, color reversal papers, etc.

For the photographic light-sensitive material according to the present invention, either a transparent support or a reflective support can be employed. The term "reflective support" as used herein means a support having an increased reflection property for the purpose of rendering dye images formed in the silver halide emulsion layer clear. Examples of the reflective support include a support having coated thereon a hydrophobic resin having a light reflective substance, such as titanium oxide, zinc oxide, calcium carbonate, calcium sulfate, etc., dispersed therein and a support composed of a hydrophobic resin having a light reflective substance dispersed therein. More specifically, they include baryta coated paper, polyethylene coated paper, polypropylene type synthetic paper, or a transparent support, for example, a glass plate, a polyester film such as a polyethylene terephthalate film, a cellulose triacetate film, a cellulose nitrate film, etc., a polyamide film, a polycarbonate film, a polystyrene film, etc. having a reflective layer or having incorporated therein a reflective substance. A suitable support can be appropriately selected depending on the purpose for use.

By the use of the magenta coupler according to the present invention, the hue of magenta images formed is easily controlled, and magenta images having high sensitivity and gradation are obtained. Further, even when a rapid color development is carried out within a period of 2 minutes and 30 seconds using a color developing solution which does not substantially contain benzyl alcohol, the maximum color density is obtained which is comparatively high to that obtained by processing with a color developing solution which contains benzyl alcohol in an amount of 15 ml per liter thereof.

The present invention is described in detail with reference to the following examples, but the present invention is not to be construed as being limited thereto.

EXAMPLE 1

To 16.8 g (0.0168 mol) of a magenta coupler, i.e., Compound M-4 were added 33.6 ml of tri(2-ethylhexy) phosphate and 42.0 ml of ethyl acetate, and the mixture was dissolved by heating. The resulting solution was added to 100 ml of an aqueous solution containing 10 g of gelatin and 1.0 g of sodium dodecylbenzenesulfonate, and the mixture was stirred at a high speed to obtain a finely emulsified dispersion. The whole of the emulsified dispersion was added to 100 g of a silver chlorobromide emulsion (having a bromide content of 50 mol % and containing 6.5 g of silver), and to the mixture was added 10 ml of a 2% aqueous solution of 2,4-dihydroxy-6-chloro-s-triazine sodium salt as a hardener. The resulting mixture was coated on a paper support both surfaces of which were laminated with polyethylene at a silver coating amount of 200 mg/m$^2$. On the emulsion layer was coated a gelatin layer to prepare a sample, which was designated Sample A.

Samples B to L were prepared in a manner similar to that described for Sample A except using Compounds M-5, M-6, M-7, M-17, M-23, M-38, M-41, M-42, M-43, M-48, and M-49 in place of Compound M-4, respectively. In these samples, the amount of the coupler was the same molar amount (i.e., 0.0168 mol) as in Sample A, the amount of tri(2-ethylhexyl) phosphate was 2 ml per gram of the coupler, and the amount of ethyl acetate was 2.5 ml per gram of the coupler. The method for preparation of an emulsified dispersion, a silver halide emulsion and an amount of thereof, a support, and the coating amount of silver were the same as in Sample A.

Further, for comparison, a sample was prepared in a manner similar to that described for Sample A except using 15.0 g (0.0168 mol) of Comparative Compound shown below in place of Compound M-4, 30.0 ml of tri(2-ethylhexyl) phosphate, and 37.5 ml of ethyl acetate. This sample was designated Comparative Sample.

Comparative Compound:

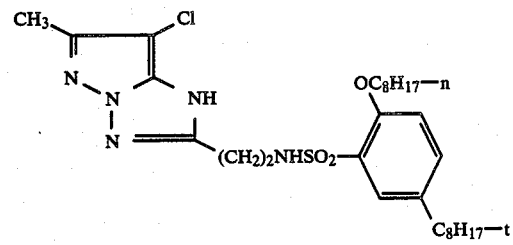

These samples (Samples A to L and Comparative Sample) were subjected to wedge exposure of 1,000 CMS and then the color development processing as shown below.

| Processing Step | Temperature (°C.) | Time |
|---|---|---|
| Color development | 33 | 3 min 30 sec |
| Bleach-fixing | 33 | 1 min 30 sec |
| Washing with water | 28–35 | 3 min |

The composition of each processing solution used in the above-described processing step was as follows.

| | |
|---|---|
| Color Developing Solution: | |
| Benzyl alcohol | 15 ml |
| Diethylenetriaminepentaacetic acid | 5 g |
| KBr | 0.4 g |
| $Na_2SO_3$ | 5 g |
| $Na_2CO_3$ | 30 g |
| Hydroxyamine sulfate | 2 g |
| 4-Amino-3-methyl-N—β-(methanesulfonamido)ethylaniline.3/2$H_2SO_4$.$H_2O$ | 4.5 g |
| Water to make | 1,000 ml |
| | pH = 10.1 |
| Bleach-Fixing Solution: | |
| Ammonium thiosulfate (70 wt %) | 150 ml |
| $Na_2SO_3$ | 10 g |
| Na[Fe(EDTA)] | 40 g |
| EDTA | 5 g |
| Water to make | 1,000 ml |
| | pH = 6.8 |

The thus-obtained magenta color image of each sample was sharp and of high saturation. The photographic characteristics of these color images were determined, and the results thus obtained are shown in Table 1.

TABLE 1

| Sample | Sensitivity* (S) | Gradation (γ) | Maximum Density (Dm) |
|---|---|---|---|
| Comparative Sample | 100 | 2.92 | 2.94 |
| A (Invention) | 70 | 3.33 | 3.01 |
| B (Invention) | 72 | 3.30 | 2.89 |
| C (Invention) | 67 | 3.25 | 2.95 |
| D (Invention) | 65 | 3.40 | 3.11 |
| E (Invention) | 80 | 3.11 | 3.09 |
| F (Invention) | 66 | 3.21 | 3.07 |
| G (Invention) | 70 | 3.30 | 2.98 |
| H (Invention) | 67 | 3.26 | 3.06 |
| I (Invention) | 69 | 3.24 | 3.05 |

TABLE 1-continued

| Sample | Sensitivity* (S) | Gradation (γ) | Maximum Density (Dm) |
|---|---|---|---|
| J (Invention) | 66 | 3.28 | 2.97 |
| K (Invention) | 70 | 3.23 | 3.04 |
| L (Invention) | 68 | 3.28 | 3.00 |

*A relative value of the exposure amount required for obtaining a density of fog +0.5 with the value for Comparative Sample being taken as 100. As the value is small, the sensitivity is high.

From the results shown in Table 1, it is apparent that the couplers according to the present invention exhibit superior characteristics in both the sensitivity and the gradation in comparison with the Comparative Compound as the coupler having an alkyl group at the 6-position. This is because the coupling activity is increased and the color forming efficiency is increased upon the introduction of a ureido group or a urethane group into the 6-position.

EXAMPLE 2

Color photographic light-sensitive materials (Samples M to R) were prepared as shown in Table 2 below by coating the first layer (lowermost layer) through the seventh layer (uppermost layer) in this order on a paper support laminated on both sides thereof with polyethylene.

The emulsified dispersion of the magenta coupler and a coating solution composition containing the same used in the third layer were prepared in the same manner as described in Example 1.

TABLE 2

| | |
|---|---|
| Support | A paper support laminated on both sides thereof with polyethylene |
| First layer (lowermost layer) | Blue-sensitive silver chlorobromide emulsion (Br: 80 mol %, Ag: 350 mg/m$^2$)<br>Gelatin (1,500 mg/m$^2$)<br>Yellow coupler (*1) (500 mg/m$^2$)<br>Solvent (*2) (400 mg/m$^2$) |
| Second layer | Gelatin (1,100 mg/m$^2$)<br>Color mixing preventing agent (*3) (200 mg/m$^2$)<br>Solvent (*4) (100 mg/m$^2$) |
| Third layer | Green-sensitive silver chlorobromide emulsion (Br: 50 mol %, Ag: 180 mg/m$^2$)<br>Magenta coupler (*5) (3.4 × 10$^{-4}$ mol/m$^2$)<br>Solvent (*6) (1 ml per gram of magenta coupler) |
| Fourth layer | Gelatin (1,600 mg/m$^2$)<br>Ultraviolet light absorbing agent (*7) (700 mg/m$^2$)<br>Color mixing preventing agent (*3) (200 mg/m$^2$)<br>Solvent (*4) (300 mg/m$^2$) |
| Fifth layer | Red-sensitive silver chlorobromide emulsion (Br: 50 mol %, Ag: 300 mg/m$^2$)<br>Gelatin (1,200 mg/m$^2$)<br>Cyan coupler (*8) (404 mg/m$^2$)<br>Solvent (*4) (250 mg/m$^2$) |
| Sixth layer | Gelatin (1,000 mg/m$^2$)<br>Ultraviolet light absorbing agent (*7) (360 mg/m$^2$)<br>Solvent (*4) (120 mg/m$^2$) |
| Seventh layer (uppermost layer) | Gelatin (1,600 mg/m$^2$) |

*1 Yellow coupler:
α-Pivaloyl-α-(2,4-dioxo-5,5'-dimethyloxazolidin-3-yl)-2-chloro-5-[α-(2,4-di-tert-pentylphenoxy)-butanamido]acetanilide
*2 Solvent:
Dioctylbutyl phosphate
*3 Color mixing preventing agent:
2,5-Dioctylhydroquinone
*4 Solvent:
Dibutyl phthalate
*5 Magenta coupler:
Sample M: Compound M-4, Sample N: Compound M-5, Sample O: Compound M-6, Sample P: Compound M-7, Sample Q: Compound M-23, and Sample R: Comparative Compound in Example 1.
*6 Solvent:
Tri(2-ethylhexyl) phosphate
*7 Ultraviolet light absorbing agent:
2-(2-Hydroxy-3-sec-butyl-5-tert-butylphenyl)-benzotriazole
*8 Cyan coupler:
2-[α-(2,4-di-tert-pentylphenoxy)butanamido]-4,6-dichloro-5-ethylphenol Three color separation filters (Blue, Green, and Red) were applied to each of the above Samples M to R, and the exposure was conducted in the same manner as described in Example 1. Then, the color development processing was carried out in the same manner as described in Example 1 except that the color developing time was changed to 2 minutes, 3 minutes and 30 seconds, or 6 minutes.

The change in the photographic characteristics due to the change in the color developing time was determined, and the results are shown in Table 3.

TABLE 3

| | | Sensitivity (S)* Developing time | | | Gradation (γ) Developing time | | | Maximum density (Dm) Developing time | | |
|---|---|---|---|---|---|---|---|---|---|---|
| Sample | Coupler | 2 min | 3 min 30 sec | 6 min | 2 min | 3 min 30 sec | 6 min | 2 min | 3 min 30 sec | 6 min |
| M | (M-4) | 87 | 71 | 68 | 3.20 | 3.21 | 3.22 | 2.65 | 2.64 | 2.65 |
| N | (M-5) | 82 | 68 | 64 | 3.25 | 3.27 | 3.24 | 2.63 | 2.63 | 2.64 |
| O | (M-6) | 84 | 70 | 66 | 3.15 | 3.20 | 3.20 | 2.62 | 2.63 | 2.64 |
| P | (M-7) | 86 | 70 | 68 | 3.19 | 3.18 | 3.19 | 2.61 | 2.61 | 2.61 |
| Q | (M-23) | 85 | 77 | 71 | 3.18 | 3.18 | 3.17 | 2.58 | 2.60 | 2.60 |
| R | (Comparative Compound) | 126 | 100 | 83 | 2.62 | 2.81 | 2.79 | 2.50 | 2.63 | 2.64 |

*A relative value of the exposure amount required for obtaining a density of fog +0.5 with the value obtained by development processing of Sample R containing the Comparative Compound with a color developing time of 3 minutes and 30 seconds being taken as 100. As the value is small, the sensitivity is high.

From the results shown in Table 3, it can be seen that the couplers according to the present invention exhibit high sensitivity and gradation, and a small reliance on the change of color developing time in sensitivity, gradation, and maximum density in comparison with the Comparative Compound as the coupler having an alkyl group at the 6-position in the case of using such in a natural color multilayer photographic material. The couplers according to the present invention are excellent in view of providing photographic characteristics the change of which is small for a short period of color developing time.

EXAMPLE 3

The reflective absorption spectra of Samples A to L and Comparative Sample (hereinafter referred to as Comparative Sample 1) which had been subjected to the color development processing as described in Example 1 were measured using a Shimadzu UV-260 type ultravioletvisible light spectrometer. Further, Comparative Samples 2, 3, 4, and 5 were prepared in the same manner as described in Example 1 except using Magenta Couplers (3), (7), (8), and (9) as described in Japanese Patent Application (OPI) No. 171956/84 and subjected to the color development processing as described in Example 1. The reflective absorption spectra of these comparative samples were also measured in the same manner as described above. The maximum absorption wavelengths these sample thus measured are shown in Table 4.

Coupler (3) described in Japanese Patent Application (OPI) No. 171956/84:

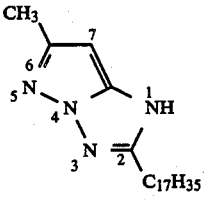

Coupler (7) described in Japanese Patent Application (OPI) No. 171956/84:

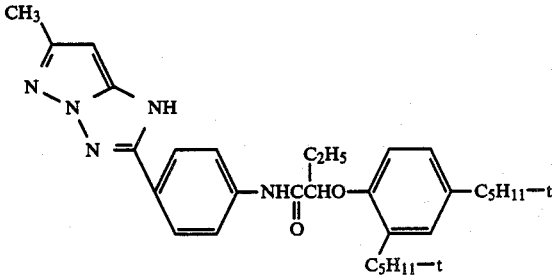

Coupler (8) described in Japanese Patent Application (OPI) No. 171956/84:

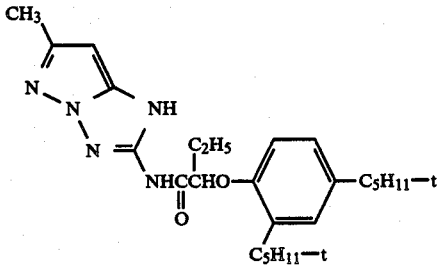

Coupler (9) described in Japanese Patent Application (OPI) No. 171956/84:

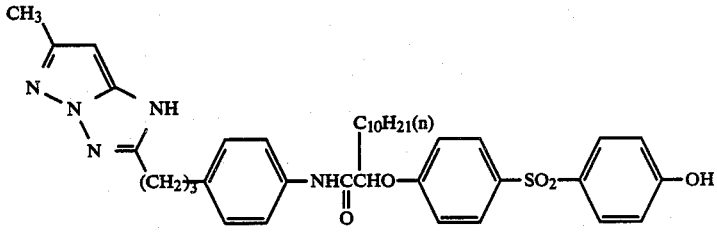

TABLE 4

| Sample | Coupler | Maximum Absorption Wavelength (nm) |
|---|---|---|
| A | M-4 (Present Invention) | 567 |
| B | M-5 (Present Invention) | 550 |
| C | M-6 (Present Invention) | 541 |
| D | M-7 (Present Invention) | 558 |
| E | M-16 (Present Invention) | 554 |
| F | M-23 (Present Invention) | 559 |
| G | M-38 (Present Invention) | 566 |
| H | M-41 (Present Invention) | 562 |
| I | M-42 (Present Invention) | 568 |
| J | M-43 (Present Invention) | 560 |
| K | M-48 (Present Invention) | 553 |
| L | M-49 (Present Invention) | 542 |
| Comparative Sample 1 | Comparative Coupler shown in Example 1* | 549 |
| Comparative Sample 2 | Coupler (3) described in Japanese Patent Application (OPI) No. 171956/84 | 538 |
| Comparative Sample 3 | Coupler (7) described in Japanese Patent Application (OPI) No. 171956/84 | 548 |
| Comparative Sample 4 | Coupler (8) described in Japanese Patent Application (OPI) No. 171956/84 | 540 |
| Comparative Sample 5 | Coupler (9) described in Japanese Patent Application (OPI) No. 171956/84 | 541 |

*covered by the scope of the claim of Japanese Patent Application (OPI) No. 171956/84.

It is apparent from the results shown in Table 4 that the change in the maximum absorption wavelength is at most about 10 nm in the cases of the comparative couplers in which the substituent at the 2-position is variously altered. On the contrary, with the couplers according to the present invention it is apparent that the maximum absorption wavelength can be changed about 30 nm by only altering the kind of the substituent attached to the nitrogen atom at the 6-position without alteration of the substituent at the 2-position. Therefore, the couplers according to the present invention are applicable to any kind of silver halide color photographic materials and can be employed in combination with a cyan coupler and a yellow coupler each having any maximum absorption wavelength by means of a minor change in the substituent thereof. Thus, the magenta couplers according to the present invention can provide the most preferred color reproducibility coupled with no subsidiary yellow absorption in the region around 430 nm as described above.

EXAMPLE 4

Samples A to L prepared in Example 1 were subjected to stepwise exposure for sensitometry through each of blue, green, and red filters using a sensitometer (an FWH type manufactured by Fuji Photo Film Co., Ltd., with a light source having a color temperature of 3,200° K.). The exposure amount was controlled so as to provide 250 CMS at an exposure time of 0.5 second. Then, these exposed samples were subjected to a color development processing according to the following processing steps.

| Processing Step | Temperature (°C.) | Time |
|---|---|---|
| Color development | 38 | 2 min 00 sec |
| Bleach-fixing | 33 | 1 min 00 sec |
| Washing with water | 24–33 | 1 min 00 sec |
| Drying | 80 | 30 sec |

The composition of each processing solution was as follows. With respect to color development, a color developing solution containing benzyl alcohol (Composition I) and a color developing solution which does not contain benzyl alcohol (Composition II) were employed.

| | Composition I | Composition II |
|---|---|---|
| Color developing solution | | |
| Diethylenetriaminepentaacetic acid | 2.0 g | 2.0 g |
| Benzyl alcohol | 15 ml | — |
| Diethylene glycol | 10 ml | — |
| $Na_2SO_3$ | 2.0 g | 2.0 g |
| KBr | 0.6 g | 0.6 g |
| Hydroxylamine sulfate | 3.0 g | 3.0 g |
| 4-Amino-3-methyl-N—ethyl-N—[β-(methanesulfonamido)ethyl]-p-phenylenediaxmine sulfate | 4.5 g | 4.5 g |
| $Na_2CO_3$ | 30.0 g | 30.0 g |
| Water to make | 1,000 ml | 1,000 ml |
| pH | 10.25 | 10.25 |
| Bleach-fixing solution | | |
| Ammonium thiosulfate (54% by weight aqueous solution) | | 150 ml |
| $Na_2SO_3$ | | 15 g |
| $NH_4$(Fe (III) (EDTA)) | | 55 g |
| EDTA.2Na | | 4 g |
| Water to make | | 1,000 ml |
| pH | | 6.9 |

The maximum density of the magenta dye images obtained according to the development processing described above in each sample was measured using a Macbeth densitometer. The results thus obtained are shown in Table 5.

TABLE 5

| Sample | Coupler | Maximum color density Composition I | Maximum color density Composition II |
|---|---|---|---|
| A | M-4 (Invention) | 2.76 | 2.65 |
| B | M-5 (Invention) | 2.65 | 2.43 |
| C | M-6 (Invention) | 2.71 | 2.65 |
| D | M-7 (Invention) | 2.86 | 2.81 |
| E | M-16 (Invention) | 2.84 | 2.80 |
| F | M-23 (Invention) | 2.82 | 2.81 |
| G | M-38 (Invention) | 2.74 | 2.70 |
| H | M-41 (Invention) | 2.81 | 2.79 |
| I | M-42 (Invention) | 2.80 | 2.75 |
| J | M-43 (Invention) | 2.73 | 2.69 |
| K | M-48 (Invention) | 2.79 | 2.75 |
| L | M-49 (Invention) | 2.76 | 2.75 |

From the results shown in Table 5 it can be understood that the maximum color densities obtained from photographic light-sensitive materials prepared by using the magenta couplers according to the present invention are almost the same in both cases wherein Composition I which contains benzyl alcohol and Composition II which does not contain benzyl alcohol are employed in the color development step.

While the invention has been described in detail and with reference to specific embodiments thereof, it will be apparent to one skilled in the art that various changes and modifications can be made therein without departing from the spirit and scope thereof.

What is claimed is:

1. A method of forming a color image comprising developing an imagewise exposed silver halide color photographic material with a developing solution containing an aromatic primary amine developing agent in the presence of at least one coupler represented by the following formula (I) or (II):

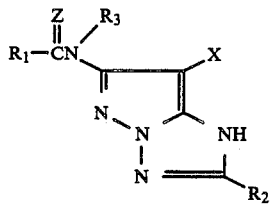

(I)

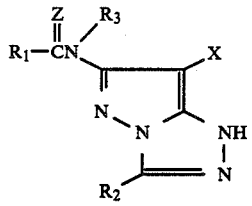

(II)

wherein $R_1$ represents a substituted or unsubstituted alkoxy group, an unsubstituted amino group, a substituted or unsubstituted alkylamino group, a substituted or unsubstituted arylamino group, or a substituted or unsubstituted N-alkylarylamino group; $R_2$ represents a monovalent substituent; $R_3$ represents a hydrogen atom, a substituted or unsubstituted alkyl group, or a substituted or unsubstituted aryl group, or $R_1$ and $R_3$ are taken together to form a ring; Z represents an oxygen atom, an imino group, or a sulfur atom; and X represents a hydrogen atom or a monovalent substituent capable of being split off upon a coupling reaction with an oxidation product of an aromatic primary amine developing agent.

2. A method of forming a color image as claimed in claim 1, wherein the substituent for the substituted alkoxy group represented by $R_1$ is selected from an alkoxy group, a halogen atom, a hydroxyl group, an aryl group, and a heterocyclic group.

3. A method of forming a color image as claimed in claim 1, wherein the substituent for the substituted alkylamino group represented by $R_1$ is selected from an alkoxy group, a hydroxyl group, and an aryl group.

4. A method of forming a color image as claimed in claim 1, wherein the substituent for the substituted arylamino group represented by $R_1$ is selected from an alkyl group, an alkoxy group, and a halogen atom.

5. A method of forming a color image as claimed in claim 1, wherein the substituent for the substituted N-alkylarylamino group represented by $R_1$ is selected from an alkoxy group, a hydroxyl group, and a halogen atom.

6. A method of forming a color image as claimed in claim 1, wherein $R_1$ represents a dialkylamino group.

7. A method of forming a color image as claimed in claim 1, wherein $R_2$ is an alkyl group substituted with a sulfonamido group, an alkyl group substituted with an acylamino group, a phenylalkyl group substituted with a sulfonamido group, a phenylalkyl group substituted with an acylamino group, an unsubstituted alkyl group, a sulfonamidophenyl group, an acylaminophenyl group, an alkoxyphenyl group, an aryloxyphenyl group, a substituted alkylphenyl group, a sulfonamidonaphthyl group, an acylaminonaphthyl group, or an unsubstituted aryl group.

8. A method of forming a color image as claimed in claim 7, wherein $R_2$ is an alkyl group substituted with a sulfonamido group, an alkyl group substituted with an acylamino group, a phenylalkyl group substituted with a sulfonamido group, a phenylalkyl group substituted with an acylamino group, or an unsubstituted alkyl group.

9. A method of forming a color image as claimed in claim 8, wherein the alkyl moiety included in the groups has from 1 to 5 carbon atoms.

10. A method of forming a color image as claimed in claim 1, wherein the monovalent substituent capable of being split off upon a coupling reaction with an oxidation product of an aromatic primary amine developing agent represented by X is a halogen atom, a carboxyl group, a group bonded to the coupling position through an oxygen atom, a group bonded to the coupling position through a nitrogen atom, or a group bonded to the coupling position through a sulfur atom.

11. A method of forming a color image as claimed in claim 1, wherein the substituent for the substituted alkyl group represented by $R_3$ is selected from an alkoxy group, a halogen atom, and an aryl group.

12. A method of forming a color image as claimed in claim 1, wherein the substituent for the substituted aryl group represented by $R_3$ is selected from a halogen atom and a nitro group.

13. A method of forming a color image as claimed in claim 1, wherein the coupler is represented by formula (I).

14. A method of forming a color image as claimed in claim 1, wherein the coupler is a bis coupler or a polymer coupler.

15. A method of forming a color image as claimed in claim 14, wherein the polymer coupler is a homopolymer composed of a polymer having a moiety represented by formula (I) or (II) or a copolymer composed of a monomer having a moiety represented by formula (I) or (II) and a non-color forming ethylenically unsaturated monomer which does not undergo coupling with the oxidation product of an aromatic primary amine developing agent.

16. A method of forming a color image as claimed in claim 15, wherein the moiety represented by formula (I) or (II) is present in a vinyl monomer.

17. A method of forming a color image as claimed in claim 16, wherein the moiety represented by formula (I) or (II) is connected to the vinyl group through a linking group represented by $R_1$ or $R_2$.

18. A method of forming a color image as claimed in claim 17, wherein the linking group represented by $R_1$ or $R_2$ is selected from a substituted or unsubstituted alkylene group, a substituted or unsubstituted phenylene group, -NHCO-, -CONH-, -O-, -OCO-, an aralkylene group, or a combination thereof.

19. A method of forming a color image as claimed in claim 17, wherein the vinyl group further has a substituent selected from a chlorine atom and a lower alkyl group having from 1 to 4 carbon atoms in addition to the coupler moiety.

20. A method of forming a color image as claimed in claim 15, wherein the non-color forming ethylenically unsaturated monomer is selected from an acrylic acid, an ester of an acrylic acid, an amide of an acrylic acid, methylene bisacrylamide, a vinyl ester, acrylonitrile, an aromatic vinyl compound, itaconic acid, citraconic acid, crotonic acid, vinylidene chloride, a vinylalkyl ether, maleic acid, maleic anhydride, an ester of maleic acid, N-vinyl-2-pyrrolidone, N-vinylpyridine, or 2- or 4-vinylpyridine.

21. A method of forming a color image as claimed in claim 14, wherein the polymer coupler is in the form of a latex.

22. A method of forming a color image as claimed in claim 1, wherein the coupler is present in the silver halide color photographic material.

23. A method of forming a color image as claimed in claim 1, wherein a processing time for the color development step is not more than 2 minutes and 30 seconds.

24. A method of forming a color image as claimed in claim 1, wherein the developing solution does not substantially contain benzyl alcohol.

25. A method of forming a color image as claimed in claim 1, wherein after the color development step, the silver halide color photographic material is subjected to either a bleaching step and then a fixing step, or a bleach-fixing step.

26. A method of forming a color image as claimed in claim 25, wherein after the fixing step or the bleach-fixing step, the silver halide color photographic material is subjected to a water-washing step or a stabilizing step.

27. A method of forming a color image as claimed in claim 26, wherein the water-washing step or the stabilizing step is carried out using a multistage countercurrent process.

28. A silver halide color photographic material comprising a support having thereon at least one silver halide emulsion layer containing at least one coupler represented by the following formula (I) or (II):

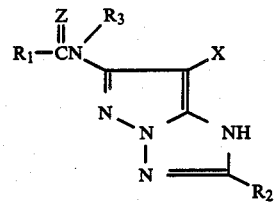

(I)

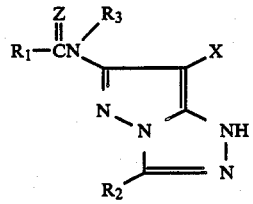

(II)

wherein $R_1$ represents a substituted or unsubstituted alkoxy group, an unsubstituted amino group, a substituted or unsubstituted alkylamino group, a substituted or unsubstituted arylamino group, or a substituted or unsubstituted N-alkylarylamino group; $R_2$ represents a monovalent substituent; $R_3$ represents a hydrogen atom, a substituted or unsubstituted alkyl group, or a substituted or unsubstituted aryl group, or $R_1$ and $R_3$ are taken together to form a ring; Z represents an oxygen atom, an imino group, or a sulfur atom; and X represents a hydrogen atom or a monovalent substituent capable of being split off upon a coupling reaction with an oxidation product of an aromatic primary amine developing agent.

29. A silver halide color photographic material as claimed in claim 28, wherein the silver halide emulsion layer is a green-sensitive silver halide emulsion layer.

30. A silver halide color photographic material as claimed in claim 29, wherein the silver halide color photographic material further contains at least one blue-sensitive halide emulsion layer and at least one red-sensitive silver halide emulsion layer.

31. A silver halide color photographic material as claimed in claim 30, wherein at least one of the blue-sensitive silver halide emulsion layers contains a yellow dye-forming coupler and at least one of the red-sensitive silver halide emulsion layers contains a cyan dye-forming coupler.

32. A silver halide color photographic material as claimed in claim 31, wherein the yellow dye-forming coupler is selected from hydrophobic α-pivaloylacetanilide type couplers and hydrophobic α-benzoylacetanilide type couplers.

33. A silver halide color photographic material as claimed in claim 31, wherein the cyan dye-forming coupler is selected from hydrophobic naphthol type couplers and hydrophobic phenol type couplers.

34. A silver halide color photographic material as claimed in claim 28, wherein the silver halide color photographic material further contains a color image stabilizing agent represented by the following formula:

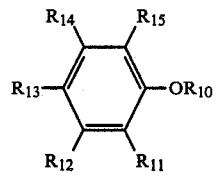

wherein $R_{10}$ represents a hydrogen atom, an alkyl group, an aryl group, or a heterocyclic group; $R_{11}$, $R_{12}$, $R_{14}$, and $R_{15}$ each represents a hydrogen atom, a hydroxyl group, an alkyl group, an aryl group, an alkoxy group, or an acylamino group; $R_{13}$ represents an alkyl group, a hydroxyl group, an aryl group, or an alkoxy group; $R_{10}$ and $R_{11}$ may be combined with each other to form a 5-membered or 6-membered ring and in such a case, $R_{12}$ represents a hydroxyl group or an alkoxy group; $R_{10}$ and $R_{11}$ may be combined with each other to form a methylenedioxy ring; and $R_{13}$ and $R_{14}$ may be combined with each other to form a 5-membered hydrocarbon ring and in such a case, $R_{10}$ represents an alkyl group, an aryl group, or a heterocyclic group.

35. A silver halide color photographic material as claimed in claim 28, wherein the support is a reflective support.

36. A method of forming a color image as claimed in claim 22, wherein said coupler is employed in an amount of from $2\times10^{-3}$ to $5\times10^{-1}$ mol per mol of silver halide.

37. A method of forming a color image as claimed in claim 36, wherein said coupler is employed in an amount of from $1\times10^{-2}$ to $5\times10^{-1}$ mol per mol of silver halide.

38. A silver halide color photographic material as claimed in claim 28, wherein said coupler is employed in an amount of from $2\times10^{-3}$ to $5\times10^{-1}$ mol per mol of silver halide.

39. A silver halide color photographic material as claimed in claim 38, wherein said coupler is employed an amount of from $1\times10^{-1}$ to $5\times10^{-1}$ mol per mol of silver halide.

40. A method of forming a color image as claimed in claim 1, wherein said coupler is added to a color developing solution in an amount of from 0.001 to 0.1 mol per liter of the solution.

41. A method of forming a color image as claimed in claim 40, wherein said coupler is added to a color developing solution in an amount of from 0.01 to 0.05 mol per liter of the solution.

* * * * *